US007947466B2

(12) United States Patent
Hansen et al.

(10) Patent No.: US 7,947,466 B2
(45) Date of Patent: May 24, 2011

(54) METHODS FOR IDENTIFYING AGENTS THAT MODULATE LGIC RECEPTOR ACTIVITY

(76) Inventors: Scott B. Hansen, La Jolla, CA (US); Palmer Taylor, Del Mar, CA (US); Zoran Radic, San Diego, CA (US)

( * ) Notice: Subject to any disclaimer, the term of this patent is extended or adjusted under 35 U.S.C. 154(b) by 766 days.

(21) Appl. No.: 10/938,370

(22) Filed: Sep. 11, 2004

(65) Prior Publication Data

US 2005/0143285 A1  Jun. 30, 2005

Related U.S. Application Data

(60) Provisional application No. 60/502,880, filed on Sep. 11, 2003.

(51) Int. Cl.
*G01N 33/483* (2006.01)
*G01N 33/52* (2006.01)

(52) U.S. Cl. ...................................... 435/7.95; 514/17.4

(58) Field of Classification Search .................. None
See application file for complete search history.

(56) References Cited

U.S. PATENT DOCUMENTS 6,388,788 B1 * 5/2002 Harris et al. .................. 359/196
6,517,781 B1 * 2/2003 Coassin et al. ................ 422/102

FOREIGN PATENT DOCUMENTS

WO    WO 01/58951    8/2001
WO    WO 03/093309   11/2003

OTHER PUBLICATIONS

Buckley C and Vincent A. Autoimmune channelopathies. Nature Clinical Practice Neurology 1(1): 22-33. (2005).*
Sadreyev et al. GenBank Accession No. AF322877 and GenPept Accession No. AAL37251. Published Dec. 2, 2001.*
(Abstract only) Angerer et al. Cell 6(1): 29-40. Published Sep. 1975.*
(Abstract only) Nelson N. Analytical Biochmistry 165(2): 287-293. Sep. 1985.*
Raines et al. Anesthesiology, 86: 476-486, Feb. 1997.*
Lukas et al. Analytical Biochemistry 301:175-188, Jan. 2002.*
Deneris et al. Clinical Chemistry 35(5): 731-737, 1989.*
Arias HR, Brain Research Reviews, 25:133-191 (1997).*
Brejc, K., van Dijk, W. J., Klaassen, R. V., Schuurmans, M., van Der Oost, J., Smit, A. B., and Sixma, T. K. (2001) *Nature* 411, 269-276.
Smit, A. B., Syed, N. I., Schaap, D., van Minnen, J., Klumperman, J., Kits, K. S., Lodder, H., van der Schors, R. C., van Elk, R., Sorgedrager, B., Brejc, K., Sixma, T. K., and Geraerts, W. P. (2001) *Nature* 411, 261-268.
Hansen, S. B., Radic, Z., Talley, T. T., Molles, B. E., Deerinck, T., Tsigelny, I., and Taylor, P. (2002) *J Biol Chem* 277, 41299-41302.

* cited by examiner

*Primary Examiner* — Daniel E Kolker
*Assistant Examiner* — Stacey MacFarlane
(74) *Attorney, Agent, or Firm* — Workman Nydegger

(57) ABSTRACT

Fluorescence based screening assays are provided that allow for the for identification of agents that selectively bind to a ligand-gated ion channel (LGIC) such as a nicotinic acetylcholine receptor (nAChR). Also provided are methods for identifying agents that selectively bind to a neuronal-type nAChR by detecting binding of the agent to an *Aplysia* AChBP, which is representative of a neuronal-type nAChR. In addition, compositions and kits for performing such methods are provided.

62 Claims, 6 Drawing Sheets

FIGURE 3

```
                                                              β1-β2 loop
                    10        20        30        40        50        60        70
                    |         |         |         |         |         |         |
Aplysia    HSQANLMRLKSDLFNRSPMYPGPTKDDPLTVTLGFTLQDIVKADSSTNEVDLVYYEQQRWKLNSLMWDPNEYGNITDF
Lymnaea       LDRADILYNIRQTSRPDVIP-TQRDRPVAVSVSLKFINILEVNEITNEVDVVFWQQTTWSDRTLA--WNSSHSPDQV
Bolinus       SHGQIRWTLLNQITGESDVIP-LSNNTPLNVSLNFKLMNILEADTEKDQVEVVLWTQASWKVPYYSS-LLSSSSLDQV
Human_α1     -EHETRLVAKLFKDYSSVVRPVEDHRQVVEVTVGLQLIQLINVDEVNQIVTTNVRLKQQWVDYNLKWNPDDYGGVKKI
Human_α7     -EFQRKLYKELVKNYNPLERPVANDSQPLTVYFSLSLLQIMDVDEKNQVLTTNIWLQMSWTDHYLQWNVSEYPGVKTV
                      *           : ..: :      . ..:            :  *           .  .  .
                                                                    Cys loop
                    80        90        100       110       120       130       140       150
                    |         |         |         |         |         |         |         |
Aplysia    RTSAADIWTPDITAYS-STRPVQVLSPQIAVVTHDGSVMFIPAQRLSFMCDPTGVDSEE-GATCAVKFGSWVYSGFEI
Lymnaea    SVPISSLWVPDLAAYN-AISKPEVLTPQLARVVSDGEVLYMPSIRQRFSCDVSGVDTES-GATCRIKIGSWTHHSREI
Bolinus    SLPASKMWTPDLSFYN-AIAAPELLSTDRVVVSKDGSVIYVPSQRVRFTCDLINVDTEP-GATCRIKVGSWTFDNKQL
Human α1   HIPSEKIWRPDLVLYNNADGDFAIVKFTKVLLQYTGHITWTPPAIFKSYCEIIVTHFPFDEQNCSMKLGTWTYDGSVV
Human_α7   RFPDGQIWKPDILLYNSADERFDATFHTNVLVNSSGHCQYLPPGIFKSSCYIDVRWFPFDVQHCKLKFGSWSYGGW--
              .   :*  **:    *              : *   * :*.   *       * .*.* *
              β8-β9 loop
                    160       170       180       190       200       210      219
                    |         |         |         |         |         |         |
Aplysia    DLKTDTD-QVDLSSYYAS-SKYEILSATQTRQVQHYSCC-PEPYIDVNLVVKFRERRAGNGFFRNLFD ⎤
Lymnaea    SVDPTTE-NSDDSEYFSQYSRFEILDVTQKKNSVTYSCC-PEAYEDVEVSLNFRKKGRSEIL------ ⎬ Soluble AChBP
Bolinus    ALITGEEGVVNIAEYFDS-PKYDLLSATQSLNRKKYRCC-ENMYEDIEITFAFRKK------------ ⎦
Human_α1   AINPESD-QPDLSNFMES-GEWVIKESRGWKHSVTYSCCPDTPYLDITYHFVMQRLPLYFIV ⎤
Human_α7   SLDLQMQ-EADISGYIPN-GEWDLVGIPGKRSERFYECC-KEPYPDVTFTVTMRRRTLYYGL ⎬ nAChR
              :          :  .            * .    *   :   . ::.
```

Figure 5A
Figure 5C
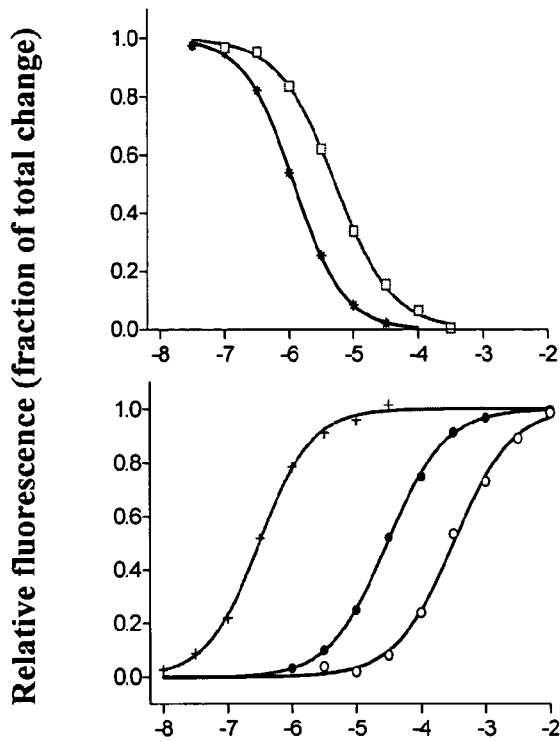
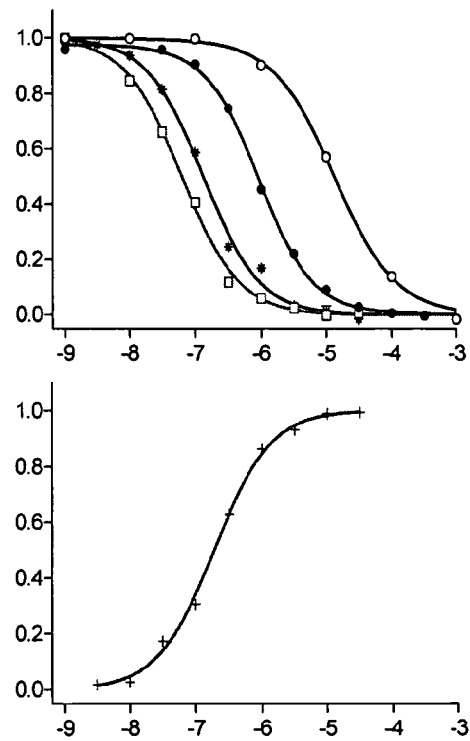
Figure 5B
Log { [ligand] (M) }
Figure 5D

SEQUENCE LISTING

```
<160> NUMBER OF SEQ ID NOS: 10

<210> SEQ ID NO 1
<211> LENGTH: 711
<212> TYPE: DNA
<213> ORGANISM: Aplysia californica

<400> SEQUENCE: 1
atgctcgtct cggtgtatct cgccctcctg gtggcctgtg tcggacaagc tcacagccaa      60
gcaaacctca tgcgcctcaa aagtgacctt tttaataggt ccccgatgta cccaggcccc     120
accaaggacg accctctgac cgtgacctta gggttcaccc tccaggacat tgtcaaggtc     180
gactcatcca cgaacgaggt ggacctagtc tactacgagc agcagagatg gaagctcaac     240
agtctcatgt gggatccaaa cgagtacggt aacatcaccg acttcaggac gtctgcggca     300
gacatctgga cacctgacat cactgcgtac agttctacaa gacctgtaca ggtcctatcc     360
ccgcagattg ctgttgtcac ccacgacggc tctgttatgt ttattcctgc caacgcctc     420 agcttcatgt gtgacccgac tggggtagac agcgaggagg gggttacgtg tgccgtgaaa    480
tttggttctt gggtatacag cgggtttgaa atagacctga aaacggacac agaccaagtg    540
gatctcagct cgtattacgc aagctccaag tacgagattc tgtcagctac tcagacccgg    600
caagttcagc actactcatg ttgccccgag ccctatatag atgtcaatct cgttgtcaag    660
tttcgcgaga ggcgggcagg gaatggcttc ttcaggaatc tctttgacta a             711

<210> SEQ ID NO 2
<211> LENGTH: 219
```

```
<212> TYPE: PRT
<213> ORGANISM: Aplysia californica

<400> SEQUENCE: 2

His Ser Gln Ala Asn Leu Met Arg Leu Lys Ser Asp Leu Phe Asn Arg
1               5                   10                  15

Ser Pro Met Tyr Pro Gly Pro Thr Lys Asp Asp Pro Leu Thr Val Thr
            20                  25                  30

Leu Gly Phe Thr Leu Gln Asp Ile Val Lys Ala Asp Ser Ser Thr Asn
        35                  40                  45

Glu Val Asp Leu Val Tyr Tyr Glu Gln Gln Arg Trp Lys Leu Asn Ser
50                  55                  60

Leu Met Trp Asp Pro Asn Glu Tyr Gly Asn Ile Thr Asp Phe Arg Thr
65                  70                  75                  80

Ser Ala Ala Asp Ile Trp Thr Pro Asp Ile Thr Ala Tyr Ser Ser Thr
                85                  90                  95

Arg Pro Val Gln Val Leu Ser Pro Gln Ile Ala Val Val Thr His Asp
            100                 105                 110

Gly Ser Val Met Phe Ile Pro Ala Gln Arg Leu Ser Phe Met Cys Asp
        115                 120                 125

Pro Thr Gly Val Asp Ser Glu Glu Gly Ala Thr Cys Ala Val Lys Phe
130                 135                 140

Gly Ser Trp Val Tyr Ser Gly Phe Glu Ile Asp Leu Lys Thr Asp Thr
145                 150                 155                 160

Asp Gln Val Asp Leu Ser Ser Tyr Tyr Ala Ser Ser Lys Tyr Glu Ile
                165                 170                 175

Leu Ser Ala Thr Gln Thr Arg Gln Val Gln His Tyr Ser Cys Cys Pro
            180                 185                 190

Glu Pro Tyr Ile Asp Val Asn Leu Val Val Lys Phe Arg Glu Arg Arg
        195                 200                 205

Ala Gly Asn Gly Phe Phe Arg Asn Leu Phe Asp
    210                 215

<210> SEQ ID NO 3
<211> LENGTH: 711
<212> TYPE: DNA
<213> ORGANISM: Aplysia californica

<400> SEQUENCE: 3
atgctcgtct cggtgtatct cgctctcctg gtggcctgtg tcggacaagc tcacagccaa      60
gcaaacctca tgcgcctcaa aagtgacctt tttaataggt ccccgatgta cccaggcccc     120
accaaggacg accctctgac cgtgacctta gggttcaccc tccaggacat tgtcaaggcc     180
gactcatcca cgaacgaggt ggacctagtc tactacgagc agcagagatg gaagctcaac     240
agtctcatgt gggatccaaa cgagtacggg aacatcaccg acttcaggac gtctgcggca     300
gacatctgga cacctgacat cactgcgtac agttctacaa gacctgtaca ggtcctatcc     360
ccgcagattg ctgttgtcac ccacgacggc tctgttatgt ttattcctgc ccaacgcctc     420
agcttcatgt gtgacccgac tggggtagac agcgaggagg gggctacgtg tgccgtgaaa     480
tttggctctt gggtatacag cgggtttgaa atagacctga aaacggacac agaccaagtg     540
gatctcagct cgtattacgc aagctccaag tacgagattc tgtcagctac tcagacccgg     600
caagttcagc actactcatg ttgccccgag ccctatatag atgtcaatct cgttgtcaag     660
tttcgcgaga ggcgggcagg gaatggcttc ttcaggaatc tctttgacta a              711
```

```
<210> SEQ ID NO 4
<211> LENGTH: 219
<212> TYPE: PRT
<213> ORGANISM: Aplysia californica

<400> SEQUENCE: 4

His Ser Gln Ala Asn Leu Met Arg Leu Lys Ser Asp Leu Phe Asn Arg
1               5                   10                  15

Ser Pro Met Tyr Pro Gly Pro Thr Lys Asp Asp Pro Leu Thr Val Thr
            20                  25                  30

Leu Gly Phe Thr Leu Gln Asp Ile Val Lys Val Asp Ser Ser Thr Asn
        35                  40                  45

Glu Val Asp Leu Val Tyr Tyr Glu Gln Gln Arg Trp Lys Leu Asn Ser
    50                  55                  60

Leu Met Trp Asp Pro Asn Glu Tyr Gly Asn Ile Thr Asp Phe Arg Thr
65                  70                  75                  80

Ser Ala Ala Asp Ile Trp Thr Pro Asp Ile Thr Ala Tyr Ser Ser Thr
                85                  90                  95

Arg Pro Val Gln Val Leu Ser Pro Gln Ile Ala Val Val Thr His Asp
            100                 105                 110

Gly Ser Val Met Phe Ile Pro Ala Gln Arg Leu Ser Phe Met Cys Asp
        115                 120                 125

Pro Thr Gly Val Asp Ser Glu Glu Gly Val Thr Cys Ala Val Lys Phe
    130                 135                 140

Gly Ser Trp Val Tyr Ser Gly Phe Glu Ile Asp Leu Lys Thr Asp Thr
145                 150                 155                 160

Asp Gln Val Asp Leu Ser Ser Tyr Tyr Ala Ser Ser Lys Tyr Glu Ile
                165                 170                 175

Leu Ser Ala Thr Gln Thr Arg Gln Val Gln His Tyr Ser Cys Cys Pro
            180                 185                 190

Glu Pro Tyr Ile Asp Val Asn Leu Val Val Lys Phe Arg Glu Arg Arg
        195                 200                 205

Ala Gly Asn Gly Phe Phe Arg Asn Leu Phe Asp
    210                 215

<210> SEQ ID NO 5
<211> LENGTH: 777
<212> TYPE: DNA
<213> ORGANISM: Artificial
<220> FEATURE:
<223> OTHER INFORMATION: synthetic construct related to Aplysia
      californica

<400> SEQUENCE: 5
atgtctgcac ttctgatcct agctcttgtt ggagctgcag ttgctgacta caaagaccat      60
gacggtgatt ataaagatca tgacatcgat tacaaggatg acgatgacaa gcttcattcc     120
caggccaacc ttatgagact gaagagcgat ctatttaaca ggagtcccat gtaccccggg     180
cctacaaaag acgacccact cactgtcaca ctcgggttca cactgcagga catcgtcaag     240
gctgatagta gcactaacga agtagatctg gtttattacg agcagcagcg gtggaaactg     300
aattcgctga tgtgggaccc caacgagtat ggcaacatta ccgatttccg tcgaagtgct     360
gccgatatct ggacgcctga catcaccgcc tactcctcta ctcgccccgt gcaggtttta     420
agtcctcaga ttgctgtggt tacccatgac ggaagcgtga tgttcattcc agcacagcga     480
ctgagcttta tgtgtgaccc caccggcgtc gattccgagg aaggagctac ttgcgctgtc     540
aaatttggat cctgggtgta cagcgggttt gaaatcgacc ttaagacgga cacagaccag     600
```

```
gtggatctca gctcctatta cgcgtccagc aagtacgaga ttctgtccgc tactcagacc    660
cggcaagtgc agcactactc ctgctgtccg gagccctata tcgatgtcaa tctcgtggtc    720
aagtttcgcg agaggcgggc agggaatggc ttcttcagga atctctttga ctcgaga       777
```

<210> SEQ ID NO 6
<211> LENGTH: 229
<212> TYPE: PRT
<213> ORGANISM: Lymnaea stagnalis

<400> SEQUENCE: 6

| Met | Arg | Arg | Asn | Ile | Phe | Cys | Leu | Ala | Cys | Leu | Trp | Ile | Val | Gln | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Cys Leu Ser Leu Asp Arg Ala Asp Ile Leu Tyr Asn Ile Arg Gln Thr
            20                  25                  30

Ser Arg Pro Asp Val Ile Pro Thr Gln Arg Asp Arg Pro Val Ala Val
        35                  40                  45

Ser Val Ser Leu Lys Phe Ile Asn Ile Leu Glu Val Asn Glu Ile Thr
    50                  55                  60

Asn Glu Val Asp Val Val Phe Trp Gln Gln Thr Thr Trp Ser Asp Arg
65                  70                  75                  80

Thr Leu Ala Trp Asn Ser Ser His Ser Pro Asp Gln Val Ser Val Pro
                85                  90                  95

Ile Ser Ser Leu Trp Val Pro Asp Leu Ala Ala Tyr Asn Ala Ile Ser
            100                 105                 110

Lys Pro Glu Val Leu Thr Pro Gln Leu Ala Arg Val Val Ser Asp Gly
        115                 120                 125

Glu Val Leu Tyr Met Pro Ser Ile Arg Gln Arg Phe Ser Cys Asp Val
    130                 135                 140

Ser Gly Val Asp Thr Glu Ser Gly Ala Thr Cys Arg Ile Lys Ile Gly
145                 150                 155                 160

Ser Trp Thr His His Ser Arg Glu Ile Ser Val Asp Pro Thr Thr Glu
                165                 170                 175

Asn Ser Asp Asp Ser Glu Tyr Phe Ser Gln Tyr Ser Arg Phe Glu Ile
            180                 185                 190

Leu Asp Val Thr Gln Lys Lys Asn Ser Val Thr Tyr Ser Cys Cys Pro
        195                 200                 205

Glu Ala Tyr Glu Asp Val Glu Val Ser Leu Asn Phe Arg Lys Lys Gly
    210                 215                 220

Arg Ser Glu Ile Leu
225

<210> SEQ ID NO 7
<211> LENGTH: 203
<212> TYPE: PRT
<213> ORGANISM: Bolinus truncatus

<400> SEQUENCE: 7

Gln Ile Arg Trp Thr Leu Leu Asn Gln Ile Thr Gly Glu Ser Asp Val
1               5                   10                  15

Ile Pro Leu Ser Asn Asn Thr Pro Leu Asn Val Ser Leu Asn Phe Lys
            20                  25                  30

Leu Met Asn Ile Leu Glu Ala Asp Thr Glu Lys Asp Gln Val Glu Val
        35                  40                  45

Val Leu Trp Thr Gln Ala Ser Trp Lys Val Pro Tyr Tyr Ser Ser Leu
    50                  55                  60

Leu Ser Ser Ser Ser Leu Asp Gln Val Ser Leu Pro Ala Ser Lys Met

```
                65                  70                  75                  80
Trp Thr Pro Asp Leu Ser Phe Tyr Asn Ala Ile Ala Ala Pro Glu Leu
                    85                  90                  95

Leu Ser Thr Asp Arg Val Val Ser Lys Asp Gly Ser Val Ile Tyr
                100                 105                 110

Val Pro Ser Gln Arg Val Arg Phe Thr Cys Asp Leu Ile Asn Val Asp
                115                 120                 125

Thr Glu Pro Gly Ala Thr Cys Arg Ile Lys Val Gly Ser Trp Thr Phe
            130                 135                 140

Asp Asn Lys Gln Leu Ala Leu Ile Thr Gly Glu Gly Val Val Asn
145                 150                 155                 160

Ile Ala Glu Tyr Phe Asp Ser Pro Lys Tyr Asp Leu Leu Ser Ala Thr
                    165                 170                 175

Gln Ser Leu Asn Arg Lys Lys Tyr Arg Cys Cys Glu Asn Met Tyr Glu
                180                 185                 190

Asp Ile Glu Ile Thr Phe Ala Phe Arg Lys Lys
            195                 200
```

<210> SEQ ID NO 8
<211> LENGTH: 289
<212> TYPE: PRT
<213> ORGANISM: Homo sapiens

<400> SEQUENCE: 8

```
Met Glu Pro Trp Pro Leu Leu Leu Leu Phe Ser Leu Cys Ser Ala Gly
1               5                   10                  15

Leu Val Leu Gly Ser Glu His Glu Thr Arg Leu Val Ala Lys Leu Phe
                20                  25                  30

Lys Asp Tyr Ser Ser Val Val Arg Pro Val Glu Asp His Arg Gln Val
            35                  40                  45

Val Glu Val Thr Val Gly Leu Gln Leu Ile Gln Leu Ile Asn Val Asp
        50                  55                  60

Glu Val Asn Gln Ile Val Thr Thr Asn Val Arg Leu Lys Gln Gly Asp
65                  70                  75                  80

Met Val Asp Leu Pro Arg Pro Ser Cys Val Thr Leu Gly Val Pro Leu
                85                  90                  95

Phe Ser His Leu Gln Asn Glu Gln Trp Val Asp Tyr Asn Leu Lys Trp
                100                 105                 110

Asn Pro Asp Asp Tyr Gly Gly Val Lys Lys Ile His Ile Pro Ser Glu
            115                 120                 125

Lys Ile Trp Arg Pro Asp Leu Val Leu Tyr Asn Asn Ala Asp Gly Asp
        130                 135                 140

Phe Ala Ile Val Lys Phe Thr Lys Val Leu Leu Gln Tyr Thr Gly His
145                 150                 155                 160

Ile Thr Trp Thr Pro Pro Ala Ile Phe Lys Ser Tyr Cys Glu Ile Ile
                    165                 170                 175

Val Thr His Phe Pro Phe Asp Glu Gln Asn Cys Ser Met Lys Leu Gly
                180                 185                 190

Thr Trp Thr Tyr Asp Gly Ser Val Val Ala Ile Asn Pro Glu Ser Asp
            195                 200                 205

Gln Pro Asp Leu Ser Asn Phe Met Glu Ser Gly Glu Trp Val Ile Lys
        210                 215                 220

Glu Ser Arg Gly Trp Lys His Ser Val Thr Tyr Ser Cys Cys Pro Asp
225                 230                 235                 240

Thr Pro Tyr Leu Asp Ile Thr Tyr His Phe Val Met Gln Arg Leu Pro
```

-continued

```
                245                 250                 255
Leu Tyr Phe Ile Val Asn Val Ile Ile Pro Cys Leu Leu Phe Ser Phe
            260                 265                 270

Leu Thr Gly Leu Val Phe Tyr Leu Pro Thr Asp Ser Gly Glu Lys Met
            275                 280                 285

Thr

<210> SEQ ID NO 9
<211> LENGTH: 246
<212> TYPE: PRT
<213> ORGANISM: Homo sapiens

<400> SEQUENCE: 9

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Asn Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Pro Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr Gly Leu Asn Leu Leu Ile Pro
225                 230                 235                 240

Cys Val Leu Ile Ser Ala
                245

<210> SEQ ID NO 10
<211> LENGTH: 742
<212> TYPE: DNA
<213> ORGANISM: Artificial
<220> FEATURE:
<223> OTHER INFORMATION: synthetic construct

<400> SEQUENCE: 10
atgtctgcac ttctgatcct agctcttgtt ggagctgcag ttgctgacta caaagaccat    60
gacggtgatt ataaagatca tgacatcgat tacaaggatg acgatgacaa gcttgaccgg   120
```

-continued

```
gcagacatcc tgtacaacat ccgccagaca tcgagaccgg atgtgattcc cacccagcgc      180 gatcgcccg  tggccgtgtc cgtctctctg aagttcatca acatcctgga agtgaacgag      240
ataaccaacg aggtggacgt ggtcttctgg cagcagacga cttggtccga caggaccctc      300
gcctggaatt ccagccacag ccccgaccag gtgtccgtgc ccatcagctc tctgtgggta      360
cctgacctcg ctgcctacaa cgccatcagc aagcctgagg tcctgacccc ccagctggca      420
cgcgtcgtgt ccgacggcga ggtgctgtac atgcctagca tccgccagcg gttctcctgc      480
gacgtgtccg gcgtcgatac ggagtccggc gccacgtgcc ggatcaagat cggttcctgg      540
acccaccact cgagggagat ttctgtggat cccactaccg agaatagcga cgacagcgaa      600
tacttctccc agtactctcg cttcgagatc ctggacgtca cacagaagaa gaactcggtg      660
acctacagct gctgtccgga ggcgtacgag gacgtggagg tgagcctcaa cttccggaag      720
aagggccgct ccgagattct ct                                               742
```

METHODS FOR IDENTIFYING AGENTS THAT MODULATE LGIC RECEPTOR ACTIVITY

CROSS REFERENCE TO RELATED APPLICATION

This application claims the benefit of priority under 35 U.S.C. §119(e) of U.S. Ser. No. 60/502,880, filed Sep. 11, 2003, the entire content of which is incorporated herein by reference.

GRANT INFORMATION

This invention was made with government support under Grant No. R37-GM 18360 awarded by the United States Public Health Service Grant. The United States government has certain rights in this invention.

BACKGROUND OF THE INVENTION

1. Field of the Invention

The invention relates generally to compositions and methods for identifying agents that selectively bind a pentameric ligand-gated ion channel, and more specifically to an acetylcholine binding protein and to soluble pentameric ligand-gated ion channel ligand binding domains; to fluorescence-based screening assays useful for identifying agents that selectively bind acetylcholine binding proteins and/or acetylcholine receptors; and to methods of detecting agents that selectively bind a neuronal-type acetylcholine receptor.

2. Background Information

Pentameric ligand-gated ion channels (LGICs), including, for example, nicotinic acetylcholine receptors (nAChRs), comprise a superfamily of neurotransmitter receptors that allow communication between cells of the central nervous system (CNS) by converting a chemical signal, in the form of a neurotransmitter released by a cell, into an electrical signal that propagates across a target cell membrane. In neuronal signaling, depolarization of adjacent regions of the neuronal membrane allows action potentials to travel down the length of the nerve cell axons as electric signals, resulting in the rapid transmission of nerve impulses over long distances. The arrival of an action potential at the terminus of a neuron typically signals the release of neurotransmitters (e.g., acetylcholine), which carry signals between cells at a synapse. Neurotransmitters released from presynaptic cells bind to receptors on the membranes of postsynaptic cells, where they act to open pentameric LGICs. The binding of acetylcholine to an acetylcholine receptor (AChR), for example, induces a conformational change in the receptor that results in an opening of a receptor-associated ion channel, allowing the passage of charged ions across the cell membrane.

The nAChRs, like all pentameric LGICs, are multisubunit proteins that mediate synaptic transmission between nerve cells, and between nerve and muscle cells, upon interaction with the neurotransmitter acetylcholine. The nAChRs, which include neuronal-type nAChRs and muscle-type nAChRs, contain five subunits that are arranged as a cylinder in the cell membrane. The nAChRs are present in a variety of tissues and control skeletal muscle contraction, and sympathetic and parasympathetic ganglia function, thereby controlling cardiovascular and visceral functions, and are important in communication pathways in the brain. These receptors are disturbed in patients with Alzheimer's disease, Parkinson's disease, schizophrenia and other disorders involving memory loss, cognitive problems and dementia. In addition, neuronal-type nAChRs are the involved in nicotine addiction.

Due to their pervasive role in CNS function, pentameric LGICs such as nAChRs provide important targets for drugs. For example, nAChR modulators are used to reduce blood pressure, and are used in surgery as neuromuscular blockers, where modulators function as competitive agonists or depolarizing agents. As such, nAChR modulating drugs have many pharmacological actions, and synthetic compounds are being examined for efficacy in a number of therapeutic indications, including, for example, in treating Alzheimer's disease, Parkinson's disease, nicotine addiction, epilepsy, attention deficit disorder and pain, and as neuroprotective agents (see, e.g., "Neuronal Nicotinic Receptors: Pharmacology and Therapeutic Opportunities", Eds. Arneric and Brioni (Wiley-Liss, Inc. 1999)).

Despite the importance of nAChR and other pentameric LGICs in nervous system function and the role of the receptors in many diseases, only a limited number of drugs are available for modulating pentameric LGIC activity. One problem in identifying agents that can selectively modulate LGIC activity is that the pentameric LGICs comprise transmembrane bound proteins, which are not readily adaptable to solution based screening assays. Thus, a need exits for screening assays that conveniently can be used to identify agents that can selectively bind a pentameric LGIC and act, for example, as an agonist or as an antagonist of the LGIC function.

SUMMARY OF THE INVENTION

The present invention is based, in part, on the discovery that changes in intrinsic fluorescence emission of an acetylcholine binding protein (AChBP) can be detected upon selective binding of a ligand to the AChBP. Such changes, which include fluorescence quenching, fluorescence enhancement, and fluorescence resonance energy transfer (FRET), provide a convenient means to detect ligand binding to an AChBP. As disclosed herein, *Aplysia* AChBP, which has characteristics of a neuronal-type nicotinic acetylcholine receptor (nAChR), including that it selectively binds α-conotoxin ImI with high affinity (Kd<100 nM), exhibits fluorescence emission due to tryptophan residues present in the region of the ligand binding site, and changes in tryptophan fluorescence emission can be detected upon selective binding of an AChR ligand. Further, the tryptophan (Trp) residues in the ligand binding site of *Aplysia* AChBP (Trp-60, Trp-86, and Trp-147) are conserved among pentameric ligand-gated ion channel (LGIC) polypeptides. Accordingly, fluorescence based screening assays are provided that allow for the for identification of agents that selectively bind to a pentameric LGIC (e.g., an nAChR). In addition, methods are provided for identifying agents that selectively bind to a neuronal-type nAChR by detecting binding of the agent to an *Aplysia* AChBP, which is representative of a neuronal-type nAChR. Compositions and kits for performing such screening assays also are provided.

The present invention relates to a method for identifying an agent that selectively binds to a pentameric LGIC. Such a method can be performed, for example, by contacting a soluble pentameric LGIC that fluoresces, with a test agent, under conditions suitable for binding of a ligand to the LGIC, and detecting a change in fluorescence of the soluble LGIC in the presence of the test agent as compared to the absence of the test agent, wherein a change in fluorescence is indicative of selective binding of the test agent to the soluble LGIC. The pentameric LGIC, for which the selectively binding agent is identified, can be any pentameric LGIC that can be expressed in a soluble form and that exhibits a change in fluorescence upon selective binding of a compound, or can be an AChBP that is representative of an LGIC polypeptide and exhibits a change in fluorescence upon selective binding of a compound. The pentameric LGIC can be a nicotinic acetylcholine receptor (nAChR), including a muscle-type nAChR or a neuronal-type nAChR; a gamma-aminobutyric acid (GABA) receptor; a glycine receptor; a glutamate receptor; or a serotonin receptor, or can be an AChBP such as an *Aplysia* AChBP (SEQ ID NO:2 or SEQ ID NO:4), or a *Lymnaea* AChBP (SEQ ID NO:6), each of which is representative of a neuronal-type AChR. A soluble LGIC useful in the present methods is exemplified by an extracellular domain of a pentameric LGIC (e.g., an extracellular domain of an nAChR) and by a soluble AChBP, as well as by peptide portions of such polypeptides that comprise the ligand binding domain and selectively bind a ligand specific for the LGIC.

A test agent useful in the present methods can be any molecule that is to be examined for the ability to selectively bind a pentameric LGIC, including test agents to be examined for agonist activity, antagonist activity, partial agonist activity, and the like. A test agent can be any molecule of interest, including, for example, a peptide, a polynucleotide, a peptidomimetic, and/or a small organic molecule. Further, the test agent can be one of a library of test agents, for example, a combinatorial library of test agents, which can be a random library, a biased library, or a variegated library, which can comprise test agents based on a general structure of a known pentameric LGIC ligand.

A method of identifying an agent that selectively binds a pentameric LGIC by contacting a test agent with a soluble LGIC can further include confirming that an identified agent selectively binds a membrane bound form of the LGIC and, further, can modulate a function of the LGIC, (e.g., the ability of ions to traverse the LGIC). As such, the present method can further include contacting the agent identified using the soluble LGIC with a membrane-bound pentameric LGIC, under conditions suitable for binding of a LGIC ligand to the membrane-bound LGIC, and detecting specific binding of the agent to the membrane-bound LGIC. In various embodiments, the soluble LGIC is a soluble nAChR, a soluble GABA receptor, a soluble glycine receptor, a soluble glutamate receptor, or a soluble serotonin receptor, or is a soluble AChBP representative of the LGIC (e.g., an *Aplysia* AChBP, which is representative of a neuronal-type nAChR), and the membrane-bound LGIC comprises an extracellular domain of an nAChR, a GABA receptor, a glycine receptor, a glutamate receptor, or a serotonin receptor, respectively. Accordingly, the invention also provides an agent identified using a method of the invention, including, for example, an agent that selectively binds an nAChR (e.g., an nAChR agonist or an nAChR antagonist), a GABA receptor, a glycine receptor, a glutamate receptor, or a serotonin receptor.

A membrane-bound pentameric LGIC can comprise a membrane fraction of cells that express the LGIC, or can comprise cells that express the membrane-bound LGIC, or can comprise artificial lipid bilayers (e.g., liposomes) to which the LGIC is bound and can selectively bind a ligand specific for the LGIC. As such, a membrane-bound pentameric LGIC (e.g., nAChR) can be an endogenous LGIC (i.e., normally expressed by the cells providing the membrane-bound LGIC), or can be an exogenous LGIC (e.g., a recombinant LGIC expressed upon introduction of an encoding polynucleotide into suitable host cells). The cells providing the membrane-bound pentameric LGIC can be any type of cells in which a functional pentameric LGIC is expressed (endogenously or exogenously), including, for example, vertebrate cells such as mammalian cells (e.g., human cells).

The present methods are based, in part, on the ability to detect a change in fluorescence due to tryptophan in the binding site of a pentameric LGIC upon selective binding of a test agent. Tryptophan absorbs ultraviolet light at about 280 nanometers (nm) and emits at about 340 nm. In one embodiment of a screening assay of the invention, the level of intrinsic tryptophan fluorescence is measured, wherein the emission spectrum is measured, for example, prior to and following contact of the soluble LGIC or AChBP with a test agent, and a change in the emission spectrum is indicative of selective binding of the test agent to the LGIC or AChBP. Such a change in intrinsic fluorescence can be fluorescence quenching (i.e., a decrease in 340 nm emission) or fluorescence enhancement (i.e., an increase in emission at or about 340 nm).

In another embodiment, fluorescence resonance energy transfer (FRET) is measured, wherein the LGIC tryptophan comprises a fluorescence donor or a fluorescence acceptor. In one aspect of this embodiment, the soluble LGIC and the test agent comprise a FRET pair, which have a FRET emission spectrum. For example, a tryptophan residue of the soluble LGIC can be the fluorescence donor, and the test agent can comprise a fluorescence acceptor that absorbs the 340 nm light (energy) emitted by the LGIC tryptophan and emits at the same or a different wavelength. The test agent can inherently absorb and/or emit fluorescent energy, or can be operatively linked to a moiety that allows the test agent to act as a fluorescence acceptor or fluorescence donor. For example, a dansyl moiety, which absorbs 340 nm light and emits at about 545 nm, can be operatively linked to the test agent(s), and the emission spectrum can be determined in the absence and in the presence of the test agent, wherein an increase in emission at 545 nm and/or a decrease in emission at 340 nm is indicative of selective binding of the test agent to the pentameric LGIC.

The present methods also can be performed in a competition assay format, wherein the soluble LGIC is contacted with an LGIC ligand, which specifically binds the LGIC, and wherein tryptophan fluorescence is enhanced or transferred to (or from) a fluorescent moiety of the LGIC ligand. In one embodiment, the competition assay is performed by contacting the soluble LGIC with an LGIC ligand that enhances tryptophan fluorescence of the LGIC. For example, gallamine, which is an nAChR ligand, can be contacted with a soluble nAChR or an AChBP, wherein fluorescence at about 340-350 nm is enhanced, and selective binding of a test agent can be identified by detecting fluorescence quenching at 340-350 nm.

In another embodiment, the competition assay is performed by contacting the soluble LGIC with a LGIC ligand (wherein the soluble LGIC and the LGIC ligand comprise a FRET pair having a FRET emission spectrum), and with a test agent, wherein selective binding of a test agent alters the FRET emission spectrum as compared to the FRET emission spectrum in the absence of the test agent; and detecting a change in the FRET emission spectrum due to binding of the test agent to the soluble LGIC. According to the present embodiment, the soluble LGIC can be a fluorescence donor (in which case the LGIC ligand comprises a fluorescence acceptor of the FRET pair), or can be fluorescence acceptor (in which case the LGIC ligand comprises a fluorescence donor of the FRET pair). Where the soluble LGIC comprises a fluorescence donor, the fluorescence acceptor can fluoresce at substantially the same wavelength as the pentameric LGIC (e.g., gallamine fluoresces at about 350 nm, which is substantially the same as the 340 nm emission of tryptophan), or can fluoresce at a different wavelength from the LGIC. Detection of a shift in the emission spectrum of the FRET pair is indicative of selective binding of the test agent to the soluble LGIC.

The present invention also relates to a method of using an AChBP that binds α-conotoxin ImI with a dissociation constant (Kd) less than 250 nanomolar (nM) and is representative of a neuronal-type nAChR to identify an agent that selectively binds the AChBP and/or a neuronal-type nAChR. Such a method can be performed, for example, by contacting a sample comprising the AChBP representative of a neuronal-type nAChR with a test agent, under conditions suitable for selective binding of a ligand to an AChBP or to a neuronal-type nAChR; and detecting selective binding of the test agent to the AChBP, thereby identifying an agent that selectively binds to the AChBP representative of a neuronal-type nAChR. An AChBP representative of a neuronal-type nAChR useful in a method of the invention can be any AChBP that has characteristics of a neuronal-type nAChR (as compared to a muscle-type nAChR), and particularly the ability to selectively bind α-conotoxin ImI with a dissociation constant (Kd) less than about 250 nM, particularly a Kd less than about 100 nM (e.g., Kd=100, 99, 90, 50, 10, 9, 5, 1, 0.9, 0.5, 0.1, 0.09 nM, or less). An AChBP representative of a neuronal-type nAChR is exemplified herein by an *Aplysia* AChBP as encoded by SEQ ID NO:1, SEQ ID NO:3, or SEQ ID NO:5 (or an oligonucleotide portion thereof that encodes a polypeptide that selectively binds an AChBP ligand), or having an amino acid sequence set forth in SEQ ID NO:2 or SEQ ID NO:4 (or an AChBP ligand binding peptide portion of said polypeptide), or can be a modified AChBP such as the *Aplysia* AChBP as set forth in SEQ ID NO:2, wherein tryptophan is substituted for tyrosine at position 55.

Selective binding of the test agent to the AChBP can be detected using any method as disclosed herein or otherwise generally used for detecting specific binding of a ligand and receptor. In one embodiment, the AChBP comprises an AChBP that fluoresces, and selective binding of the test agent is detected by detecting a change in fluorescence (emission spectrum) of the sample in the presence of the test agent as compared to the fluorescence (emission spectrum) in the absence of the test agent. The change in fluorescence can be detected using methods as disclosed herein. In one aspect, the change in fluorescence detected is a change in intrinsic fluorescence of the AChBP (e.g., fluorescence quenching). In another aspect, the test agent comprises a fluorescent moiety, wherein the AChBP and the test agent comprise a FRET pair having a FRET emission spectrum, and wherein detecting a change in fluorescence comprises detecting the FRET emission spectrum. The test agent can be a molecule that absorbs and/or emits energy at an appropriate wavelength, such that it can act as a fluorescence acceptor or fluorescence donor with respect to the AChBP tryptophan fluorescence, or can be modified to contain an operatively linked fluorescent moiety (e.g., a dansyl moiety).

Selective binding of the test agent also can be performed using a fluorescence based competition assay format, wherein an AChBP ligand is contacted with the AChBP (which fluoresces), and a change in fluorescence is detected upon competition of the test agent with the ligand and selective binding of the test agent. In one aspect, the AChBP ligand is a ligand such as gallamine, which binds to the AChBP and enhances the 340 nm tryptophan fluorescence (gallamine fluorescence emission is at 350 nm) of the AChBP, wherein selective binding of a test agent results in fluorescence quenching. In another aspect, the AChBP ligand and AChBP comprise a FRET pair, which have a FRET emission spectrum, wherein selective binding of a test agent to the AChBP alters the FRET emission spectrum as compared to the FRET emission spectrum in the absence of the test agent; and wherein a change in the FRET emission spectrum is indicative of selective binding of the test agent.

In another embodiment, selective binding of the test agent to the AChBP is detected using a scintillation proximity assay. In one aspect of this embodiment, the test agent contains a radiolabel, and the AChBP is bound to a solid support comprising a scintillant, wherein, upon selective binding to the AChBP, the radiolabel causes scintillation of the scintillant. As such, detecting scintillation of the sample is indicative of selective binding of the test agent to the AChBP. In another aspect, the scintillation proximity assay is performed in a competition format using a radiolabeled ligand, wherein a test agent that selectively binds to the AChBP results in decreased scintillation.

Upon identifying an agent that selectively binds an AChBP representative of a neuronal-type nAChR, the agent can then be examined for selective binding to a neuronal-type nAChR. Such a method can be performed, for example, by contacting a neuronal-type nAChR with the agent under conditions suitable for binding of an nAChR ligand to the neuronal-type nAChR, and detecting selective binding of the agent to the nAChR, thereby identifying a neuronal-type nAChR ligand. The neuronal-type nAChR can be a soluble nAChR, or a membrane-bound nAChR, and detection of selective binding can be detected using methods as disclosed herein or otherwise known in the art. Accordingly, the present invention also provide an agent identified by the present method, wherein the agent selectively binds an AChBP representative of a neuronal-type nAChR and/or selectively binds a neuronal-type nAChR (e.g., a neuronal-type nAChR agonist, or a neuronal-type nAChR antagonist).

The methods of the invention can be performed in a high throughput format, wherein one or a plurality of test agents and/or one or a plurality of soluble ligand-gated ion channels (LGICs) are examined in parallel. In one embodiment, a plurality of test agents (e.g., a combinatorial library of test agents) is examined for selective binding to a soluble LGIC (or to an AChBP). In another embodiment, one or more test agents are examined for selective binding to at least two different pentameric LGICs (e.g., a muscle-type nAChR and a neuronal-type nAChR; or a nAChR and a GABA receptor) and/or AChBPs and/or a combination of LGIC(s) and AChBP(s). Advantages of performing the present methods in a high throughput format include, for example, that duplicates, triplicates, or more of an assay can be performed, whereby statistically significant results can be obtained; and that one or more (positive and/or negative) controls can be performed in parallel, thus providing a means to obtain standardized results (e.g., among samples performed at different times or under different conditions).

The present invention also relates to a polynucleotide having a sequence as set forth in SEQ ID NO:5, which encodes an AChBP. As disclosed herein, a polynucleotide of the invention encodes a polypeptide as set forth in SEQ ID NO:2, which is encoded in nature by the polynucleotide as set forth in SEQ ID NO:1. As compared to SEQ ID NO:1, the polynucleotide of the invention has been modified such that it encodes an RNA molecule comprising codons that are preferentially translated in a mammalian cell. Accordingly, the invention also provides vectors containing a polynucleotide as set forth in SEQ ID NO:5 (e.g., expression vectors), and further provides host cells containing such vectors.

The present invention also relates to kits useful for practicing the present methods. A kit of the invention can contain, for example, at least one soluble LGIC that fluoresces and/or at least one AChBP that fluoresces; and can further contain at least one ligand specific for the LGIC(s) and/or AChBP(s), wherein the ligand comprises a fluorescent moiety, and the soluble LGIC and LGIC ligand (or AChBP and AChBP ligand) comprise a FRET pair. In one embodiment, the soluble LGIC(s) and/or the AChBP(s) comprises one of a plurality of soluble LGICs and/or AChBPs. The soluble LGIC and/or AChBP of the kit (or a plurality thereof) can be provided in a free (isolated) form, or can be associated with a support. For example, each of a plurality of soluble LGICs and/or AChBPs can be contained in wells of a multi-well plate (e.g., a 96 well or 384 well plate), or can be coupled to a glass slide or a silicon wafer, and can be arranged in an array (e.g., an addressable array). Such compositions, wherein LGICs and/or AChBPs of the plurality are the same or different, conveniently can be used in high throughput format type assays.

BRIEF DESCRIPTION OF THE DRAWINGS

FIG. 2A shows gallamine (□) and acetylcholine (○), which, at the designated concentrations, were reacted with 20 nM AChBP in an Applied Photophysics SX.18MV stopped-flow spectrofluorimeter; the fluorescence signal recorded. Excitation was at 280 nm, and a cut-off filter at 305 nm was used on the emission side. The first order rate constant $k_{obs}$ was plotted against ligand concentration. The individual rate constants were obtained from $k_{obs}=k_1[L]+k_{-1}$, where $k_1$ is the slope and $k_{-1}$ the ordinate intercept.

FIG. 2B illustrates typical traces showing the observed fluorescence during and after stoppage of flow. The flow time between the mixing and observation chambers is ~1 ms. The increase in fluorescence associated with gallamine binding and decrease associated with acetylcholine binding are shown in the top and bottom traces.

FIG. 2C illustrates kinetics of the fast and slow phases of α-bungarotoxin association with unliganded AChBP. Kinetics for the fast phase (○) were calculated as described above, whereas the apparent concentration independence of the slow phase (Δ) yields a limiting value of $0.34\ s^{-1}$.

FIG. 2D provides traces for the three bungarotoxin concentrations shown in FIG. 2C.

FIG. 3 shows alignments of AChBP and nAChR protein sequences. Soluble binding proteins from *Lymnaea stagnalis* (SEQ ID NO:6), *Aplysia californica* (SEQ ID NO:2) and *Bolinus truncates* (SEQ ID NO:7) are aligned with the first 210 amino acid residues of human nAChR α1 (SEQ ID NO:8) and α7 (SEQ ID NO:9) subunits. Numbering corresponds to the *Aplysia* numbering system, beginning with the first synthesized residue in the cDNA sequence (SEQ ID NO:5) and a putative start site (based on consensus sequences). Asterisks indicate identity among the receptor family; colons and periods indicate limited conservation in the series. Bold residues are conserved among soluble AChBP's, but are distinct from transmembrane spanning receptors. Underscored alanine residues at positions 43 and 138 were valine residues in an AChBP sequence isolated from a sensory cell *Aplysia* cDNA library (see Example 2).

FIGS. 5A to 5D illustrate steady state of ligand binding to *Aplysia* AChBP (FIGS. 5A and 5B) and *Lymnaea* AChBP (FIGS. 5C and 5D). Ligand binding was monitored in a 96 well fluorescent plate reader. Samples were excited at 280 nm and intrinsic tryptophan fluorescence emission was monitored at 340 nm. (○ carbachol, ● acetylcholine, + gallamine, *dansylcholine $C_6$, □ nicotine). FIGS. 5A and 5B illustrate ligand binding in *Aplysia* AChBP; FIGS. 5C and 5D illustrate ligand binding in *Lymnaea* AChBP.

DETAILED DESCRIPTION OF THE INVENTION

Figure 1:
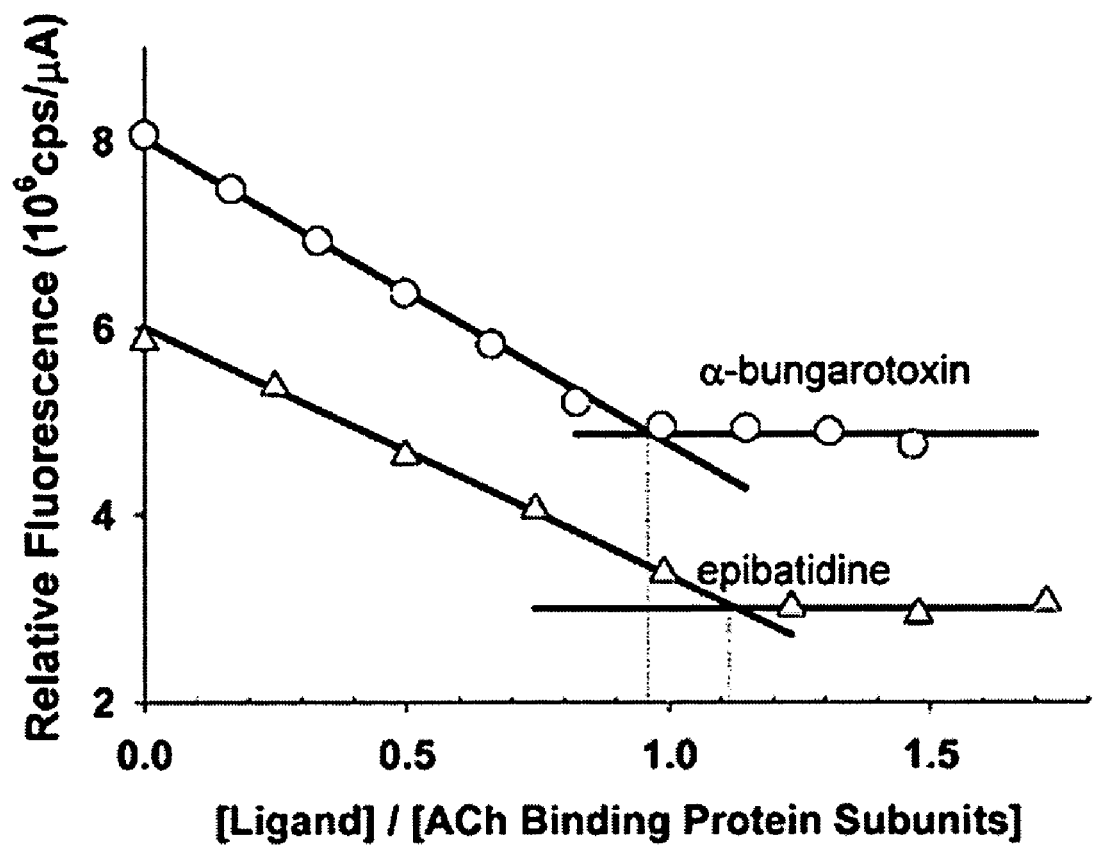
FIG. 1 shows equilibrium titration of AChBP with α-bungarotoxin (circles) or epibatidine (triangles; see Example 1).

The present invention is based on the characterization of ligand binding properties of acetylcholine binding proteins (AChBPs) from the fresh water snail, *Lymnaea stagnalis*, and the salt-water mollusk, *Aplysia californica*, and the discovery that changes in intrinsic fluorescence emission of an AChBP can be detected upon selective binding of a ligand to the AChBP. As disclosed herein, AChBPs are intrinsically fluorescent due to tryptophan residues present in the region of the ligand binding site, and changes in tryptophan fluorescence emission are detectable upon selective binding of a ligand. The tryptophan residues present in the ligand binding site of *Aplysia* AChBP are highly conserved among ligand-gated ion channels (LGICs), indicating that fluorescence based assays as exemplified herein using AChBPs similarly can be performed using LGICs and soluble ligand binding domains of LGICs. As further disclosed herein, AChBPs are suitable for use as surrogates for nicotinic acetylcholine receptors (nAChRs) and other LGICs that are of paramount importance in human pharmacology. *Aplysia* AChBP, for example, has characteristics of a neuronal-type nAChR, including high affinity α-conotoxin ImI binding activity, and, therefore, provides a model system representative of a neuronal-type nAChR. Accordingly, fluorescence based screening assays are provided that permit identification of agents that selectively bind to a pentameric LGIC including, for example, a neuronal-type AChR and/or a muscle-type nAChR, as are compositions and kits useful for performing the methods of the invention.

The nAChRs are prototype molecules for the LGIC superfamily (1, 2, 29). The nAChR was the first neurotransmitter receptor characterized as a molecular entity due, in part, to its abundance in the electric organs of *Torpedo* sp. and the finding that peptide toxins from elapid venoms bind with high affinity (30-32). The nAChR from Torpedo, similar to the receptor found in skeletal muscle throughout the fish and mammal phyla, assembles as a pentamer composed of four distinct subunits with one of the subunits expressed as two copies. The two binding sites, which are not identical in recognition characteristics in the muscle-type nAChR, reside at the interface of the α subunit and its partnering subunits. At least 12 nicotinic receptor subunits from mammalian neuronal tissues have been isolated, and determined to assemble in selected permutations of α and β subtypes. The simplest subtypes structurally are the homomeric pentamers of α subunits, such as those from the α7 subunit (2).

The nAChRs, like other LGICs, span the membrane multiple times, and function as ligand gated ion channels. The four transmembrane spans on each of the five subunits create a substantial region of hydrophobicity that makes solubilization and facile crystallization of this protein difficult. Recent electron microscopy reconstruction analysis has led to a structure of the transmembrane region resolved to four angstroms, and a description of the extracellular domain at somewhat lower resolution (33).

The acetylcholine binding protein (AChBP), a soluble protein found in the synapses of snails, is a homolog of the ligand binding domain of the nAChR. AChBP from the fresh water snail *Lymnaea stagnalis* has been characterized, crystallized, and its structure determined (3, 4). The crystal structure shows features predicted from a host of affinity labeling, site-specific mutagenesis, and subunit assembly studies conducted on the nAChR (1, 2, 5). The *Lymnaea* AChBP is pentameric, similar to other LGICs, and is composed of identical subunits that resemble the extracellular domain of the α7 receptor in neurons (i.e., neuronal-type AChR). Although *Lymnaea* AChBP shares ligand recognition characteristics with mammalian homologs, such as the pentameric α7 receptor (4), details on its ligand specificity, binding kinetics, and conformational changes have not yet been reported.

In order to ascertain whether the *Lymnaea* AChBP has the recognition properties and conformational states such that it can be a suitable functional or structural surrogate of the extracellular domain of the AChR, the AChBP was expressed in a mammalian system from a chemically synthesized cDNA of 637 bp. The cDNA encoding the *Lymnaea* AChBP was constructed by ligating a series of chemically synthesized oligonucleotides into an expression construct and expressed for analysis of ligand recognition and structural properties in solution. *Lymnaea* AChBP showed a ligand specificity similar to the nAChR and is a useful nAChR surrogate (see Example 1). Furthermore, upon ligand binding, AChBP showed major changes in fluorescence emitted from five tryptophan residues on each subunit, providing an intrinsic detection system to monitor the stoichiometry and kinetics of ligand binding. (See Example 1; see also, Hansen et al. (2002) *J. Biol. Chem.* 277: 41299-41302, which is incorporated herein by reference).

Sequences of candidate AChBPs are present in databases of invertebrate species. As further disclosed herein, an AChBP from a salt-water mollusk, *Aplysia californica*, was expressed and characterized Although the *Aplysia* AChBP sequence shares the hallmark features characteristic of the *Lymnaea* protein, as well as vertebrate nAChRs, the *Lymnaea* and *Aplysia* AChBPs come from evolutionary distant species and show only 33% amino acid residue identity (see FIG. 3). Upon purification, the *Aplysia* AChBP revealed structural and ligand recognition properties distinct from the *Lymnaea* protein, thus allowing an analysis of the two AChBPs. The *Aplysia* AChBP, similar to the *Lymnaea* AChBP, exhibited changes in tryptophan fluorescence upon ligand binding. The magnitude of the changes in fluorescence differed between the two AChBPs and certain ligands demonstrated marked differences in affinities for the two AChBPs, thereby providing distinguishing or signature ligand binding. As such, the *Aplysia* and *Lymnaea* AChBPs are useful as discrete surrogates for the extracellular domains of distinct nAChR subtypes, including muscle-type nAChRs and neuronal-type nAChRs, respectively (see Example 2; see also, Hansen et al. (2004) *J. Biol. Chem.* 279: 24197-24202, which is incorporated herein by reference).

Accordingly, the present invention provides methods for identifying an agent that selectively binds to a pentameric LGIC. Such screening assays of the invention can be performed, for example, by contacting a soluble pentameric LGIC that fluoresces, with a test agent, under conditions suitable for selective binding of a ligand to the pentameric LGIC, and detecting a change in fluorescence of the soluble LGIC in the presence of the test agent as compared to the absence of the test agent, wherein a change in fluorescence is indicative of selective binding of the test agent to the soluble LGIC. Pentameric LGICs are composed of five subunits, each of which comprises α-carbon chains that traverse the membrane four times (1, 2). Pentameric LGICs are also referred to as Cys-loop receptors because the amino-terminal, extracellular portions of LGIC subunits contain a pair of disulfide bonded cysteines separated by about 13 residues. Unless specifically indicated otherwise, the term "LGIC" or "ligand gated ion channel" means a "pentameric LGIC". Similarly, unless indicated otherwise, the term "soluble LGIC" or "membrane-bound LGIC" refers to a soluble pentameric LGIC or a membrane-bound pentameric LGIC, respectively.

A pentameric LGIC useful in the present methods can be any pentameric LGIC that can be expressed in a soluble form, selectively binds a ligand that is specifically bound by the intact LGIC, and exhibits a change in fluorescence upon selective binding of a compound (e.g., the LGIC ligand, or a test agent). An AChBP that is representative of an LGIC polypeptide, including that selectively binds a ligand specific for the LGIC and exhibits a change in fluorescence upon selective binding of a compound, also can be used in the present methods. For convenience of discussion, an AChBP having such characteristics of a pentameric LGIC is considered to be encompassed with the general meaning of the term "LGIC" or "ligand-gated ion channel". As such, the pentameric LGIC can be a nAChR (e.g., a muscle-type nAChR or a neuronal-type nAChR), a gamma-aminobutyric acid (GABA) receptor, a glycine receptor, a glutamate receptor, or a serotonin receptor, or can be an AChBP such as an *Aplysia* AChBP (see SEQ ID NOS:2 and 4), which is representative of a neuronal-type nAChR, or a *Lymnaea* AChBP (see SEQ ID NO:6; see, also, WO 01/158951; Brejc et al., *Nature* 411: 269, 2001; Smit et al., *Nature* 411: 261, 2001, each of which is incorporated herein by reference).

A soluble LGIC useful in the present methods is distinguished from a membrane-bound LGIC in that the soluble LGIC assumes a proper ligand binding conformation under aqueous conditions. Soluble LGICs can include, for example, an extracellular domain of a pentameric LGIC that retains selective ligand binding activity characteristic of the naturally occurring (membrane-bound) LGIC, but lacks the transmembrane region (domain). A soluble LGIC also can lack the intracellular domain of an intact (e.g., naturally occurring) LGIC. In addition to an extracellular domain of a pentameric LGIC, a soluble LGIC useful in the present methods is exemplified by an AChBP, as well as by peptide portions of an extracellular domain of an LGIC and of an AChBP that comprises the ligand binding domain, selectively binds a ligand specific for the intact LGIC or AChBP, and exhibits a change in fluorescence upon such selective binding.

As used herein, the term "LGIC ligand" refers to a molecule that is known to selectively bind to an LGIC. For purposes of the present invention, an LGIC ligand can be useful as a control, for example, to confirm that conditions under which a screening assay is performed are suitable for identification of an agent that selectively binds an LGIC, and can be useful in performing a competition assay. For example, where the LGIC is a nAChR, GABA receptor, glycine receptor, glutamate receptor or a serotonin receptor, a LGIC ligand can respectively include acetylcholine, GABA, glycine, glutamate, or serotonin. A ligand that selectively binds a LGIC can act as an agonist, an antagonist, a partial agonist of the LGIC, or the like. As used herein, the term "agonist" refers to a ligand that can specifically bind to a LGIC and thereby result in an increased activity by a LGIC. The term "partial agonist" is used herein to refer to a molecule that has an effect similar to, but less than, that of an agonist. The term "antagonist" is used herein to refer to a ligand that can competitively bind to a LGIC at substantially the same site as an agonist, but that does not result in an increased activity by an LGIC. For example, where the LGIC is a nAChR or a AChBP, the LGIC ligand can be a cholinergic agonist such as choline, carbachol, nicotine, or epibatidine, or an antagonist such as α-bungarotoxin (an irreversible antagonist) or d-tubocurarine (a competitive antagonist). LGIC ligands can further include, for example, a small molecule such as gallamine, which fluoresces at substantially the same wavelength as tryptophan (350 nm v. 340 nm, respectively), or a small molecule comprising a dansyl moiety (e.g., dansyl-C6-choline; see, also, Examples 1 and 2).

It should be recognized that conotoxin also can selectively bind particular pentameric LGICs, including neuronal-type nAChR comprising an α7 subunit and, as disclosed herein, *Aplysia* AChBP. More specifically, α-conotoxin ImI binds *Aplysia* AChBP with a Kd of about 0.88 nM, as compared with a Kd of about 220 nM for the neuronal-type nAChR α7 subunit (see Johnson et al., (1995) *Mol. Pharmacol.* 48, 194-199, which is incorporated herein by reference). In comparison, α-conotoxin ImI binds with a Kd of about 51 μM with muscle-type nAChR, which compares with a Kd of about 14 μM for *Lymnaea* AChBP (see Table 4). As such, the *Aplysia* AChBP can be readily distinguished from the *Lymnaea* AChBP, and further provides a useful model for neuronal-type nAChRs, which bind α-conotoxin ImI with high affinity (i.e., in the nM range). Accordingly, in one embodiment, the invention provides peptide portions of *Aplysia* AChBP (SEQ ID NO:2) that selectively binds α-conotoxin ImI, including peptide portions that selectively bind α-conotoxin 1 ml and an AChBP ligand.

As used herein, the term "selectively binds" or "specifically binds" refers to two (or more) molecules that form a complex that is relatively stable under physiologic conditions or conditions suitable for binding. The term is used herein in reference to various interactions, including, for example, the association of an agent (or of a ligand) and a pentameric LGIC. Two molecules that specifically associate can be characterized by a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or greater.

Selective binding can occur, and is stable, for example under physiological conditions, including, for example, conditions that occur in a living individual such as a human or other vertebrate or invertebrate, as well as conditions that occur in a cell culture such as used for maintaining mammalian cells or cells from another vertebrate organism or an invertebrate organism. It will be understood that selective ligand binding (or agent binding) to a pentameric LGIC occurs under conditions suitable for LGIC polypeptides to form a functional receptor conformation. Various examples of conditions suitable for selective ligand binding, as well as methods of determining such conditions, are disclosed herein (see Examples 1 and 2) or otherwise known in the art.

The methods of the invention provide a means to screen test agents in order to identify agents that selectively bind to a soluble LGIC. As used herein, the term "test agent" refers to any molecule that is to be examined for the ability to selectively bind a pentameric LGIC. Such test agents can be examined, for example, for agonist activity, antagonist activity, partial agonist activity, and the like. The term "agent" is used to herein to refer to a test agent that is identified, according to the present methods, as having the ability to selectively bind an LGIC and/or AChBP.

A test agent can be any type of molecule, including, for example, a polynucleotide, a peptide, a peptidomimetic, peptoids such as vinylogous peptoids, or a small organic molecule, and can be a naturally occurring molecule or a synthetic molecule. Polynucleotides, for example, are known to specifically interact with proteins and, therefore, can be useful as test agents to be screened for the ability to selectively bind to a ligand-gated ion channel. The term "polynucleotide" is used broadly herein to mean a sequence of two or more deoxyribonucleotides or ribonucleotides that are linked together by a phosphodiester bond. As such, the term "polynucleotide" includes RNA and DNA, which can be a synthetic RNA or DNA sequence, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, a polynucleotide useful as a test agent can contain nucleoside or nucleotide analogs, or a backbone bond other than a phosphodiester bond.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22: 5220-5234, 1994; Jellinek et al., *Biochemistry* 34: 11363-11372, 1995; Pagratis et al., *Nature Biotechnol.* 15: 68-73, 1997, each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22: 977-986, 1994; Ecker and Crooke, *BioTechnology* 13: 351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

A peptide also can be useful as a test agent to screen for the ability to selectively bind a pentameric LGIC. The term "peptide" is used broadly herein to mean two or more amino acids linked by a peptide bond. Generally, a peptide useful in a method of the invention contains at least about two, three, four, five, or six amino acids, and can contain about ten, fifteen, twenty or more amino acids. As such, it should be recognized that the term "peptide" is not used herein to suggest a particular size or number of amino acids comprising the molecule, and that a peptide of the invention can contain up to several amino acid residues or more. Generally, however, smaller peptides are preferred where an identified agent is to be further examined, for example, for use as a drug for treating a subject.

A peptide test agent can be prepared, for example, by a method of chemical synthesis, or can be expressed from a polynucleotide using recombinant DNA methodology. Where chemically synthesized, peptides containing one or more D-amino acids, or one or more amino acid analogs, for example, an amino acid that has been derivatized or otherwise modified at its reactive side chain, or in which one or more bonds linking the amino acids or amino acid analogs is modified, can be prepared. In addition, a reactive group at the amino terminus or the carboxy terminus or both can be modified. Such peptides can be modified, for example, to have improved stability to a protease, an oxidizing agent or other reactive material the peptide may encounter in a biological environment, and, therefore, can be useful for performing in vitro and/or in vivo procedures. Of course, the peptides can be modified to have decreased stability in a biological environment such that the period of time the peptide is active in the environment is reduced.

The methods of the invention include contacting a test agent with a soluble LGIC that fluoresces and detecting a change in the soluble LGIC fluorescence upon selective binding of the agent. The fluorescence of the soluble LGIC can comprise intrinsic fluorescence emission due to the presence of tryptophan residues in the protein. Tryptophan residues absorb ultraviolet light at about 280 nm and emit at about 340 nm. Tryptophan residues occur naturally in a conserved manner in many LGICs. Tryptophan residues present in the ligand binding site of an LGIC include Trp-60, Trp-86, and Trp-147 in *Aplysia* AChBP (SEQ ID NO:2), and are conserved at similar positions in other LGICs (see, e.g., FIG. 3). In addition, one or more tryptophan residues can be introduced into an LGIC using a method such as site-directed mutagenesis. For example, an LGIC such as the *Aplysia* AChBP (SEQ ID NO:2) can be mutated to include tryptophan residue(s) corresponding to *Lymnaea* AChBP Trp-53 and/or Trp-65 (see SEQ ID NO:6; corresponding to positions 55 and 69 using *Aplysia* numbering; see FIG. 3). In another example, a tyrosine residue in the agonist binding pocket of a GABA receptor can be mutated to a tryptophan residue.

As disclosed herein, a change in fluorescence of the pentameric LGIC can be detected upon selective binding of a test agent to the LGIC. Accordingly, the present methods utilize the intrinsic fluorescence of tryptophan in the region of the binding site of an LGIC and the ability to detect a change in fluorescence upon selective binding of a test agent. The level of intrinsic tryptophan fluorescence can be measured, for example, prior to and following contact of a soluble LGIC with a test agent, or a standardized level of intrinsic fluorescence of the LGIC in the absence of ligand binding can be determined. The detection of change in the emission spectrum of the LGIC upon contact with a test agent is indicative of selective binding of the test agent to the LGIC. Further, the change is proportional to the amount of agent selectively bound to the LGIC, and the degree of the change in fluorescence can vary depending on the affinity of an agent for the LGIC. For example, high affinity ligands can effect fluorescence at low concentrations. Such a change in intrinsic fluorescence can include enhancement or quenching (e.g., an increase or decrease, respectively, in 340 nm emission), and/or can be accompanied by a shift in the fluorescence emission spectra (e.g., a decrease in 340 nm emission and an increase in 545 nm emission).

Selective binding of an agent to an LGIC also can be detected using fluorescence resonance energy transfer (FRET). FRET is a distance-dependent interaction between the electronic excited states of two fluorescent molecules, wherein excitation energy is transferred from a fluorescence donor molecule to a fluorescence acceptor molecule without emission of a photon. A FRET pair includes a fluorescent donor molecule and a fluorescent acceptor molecule. For FRET to occur, the fluorescence emission spectrum of the donor and that of the acceptor must overlap, and the donor and acceptor must be in close proximity. The distance between donor and acceptor at which 50% of donors are deactivated (i.e., do not emit photons due to transfer energy to the acceptor) is defined by the Forster radius, which typically is about 10-100 angstroms. Changes in the fluorescence emission spectrum of FRET pairs can be detected, and are indicative of changes in the number of donors and acceptors that are in close proximity. Compositions and methods for using FRET with polypeptides are routine and well known (see, e.g., U.S. Pat. No. 6,737,244, which is incorporated herein by reference).

In one embodiment, the soluble LGIC and the test agent comprise a FRET pair, wherein a change in LGIC fluorescence emission is detected upon selective binding of the test agent to the LGIC. The tryptophan residues of the pentameric LGIC can function as either FRET donors or FRET acceptors. The change in fluorescence due to binding of the agent and FRET with the LGIC tryptophan(s) can include enhancement or quenching of the tryptophan fluorescence, and can include a shift in the fluorescence emission spectra. (see Example 1, Example 2).

In one aspect of FRET, a fluorescent donor molecule and a non-fluorescent acceptor molecule ("quencher") can be employed. In this application, fluorescent emission of the donor increases when quencher is displaced from close proximity to the donor, and fluorescent emission decreases when the quencher is brought into close proximity to the donor. For example, a non-fluorescent quencher can be a small cholinergic agonist, which can be contacted with a pentameric LGIC. Selective binding of the small cholinergic agonist can be detected by measuring LGIC fluorescence in the presence and the absence of the agonist, wherein a decreased LGIC fluorescence in the presence of the agonist is indicative of selective binding.

A test agent (or LGIC ligand) can fluoresce inherently (e.g., due to its structure or composition) or can be operatively linked to a fluorescent moiety (e.g., a dansyl moiety). As used herein, the term "operatively linked" or "operatively associated" means that two or more molecules are positioned with respect to each other such that they act as a single unit, with each molecule maintaining a function attributable to one or both molecules or a combination thereof. For example, where a FRET molecule (i.e., a fluorescence donor or a fluorescence acceptor) comprises a peptide LGIC ligand operatively linked to a fluorescent moiety such as dansyl, the LGIC ligand maintains it ability to selectively bind its cognate LGIC, and fluorescent moiety maintains its fluorescence characteristics. Similarly, a test agent can be operatively linked to a fluorescent moiety such that the test agent and the fluorescent moiety each retains its general characteristics.

Fluorescent moieties useful as fluorescent labels or as a fluorescent acceptor or donor of a FRET pair are well known and include, for example, fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Other potential FRET donor or acceptor molecules are known in the art (see, e.g., U.S. Pat. Nos. 5,866,336 and 6,737,244, each of which is incorporated herein by reference; see, also, Examples 1 and 2).

In one aspect, the present methods can be performed in a competition assay format, wherein a known LGIC ligand and a test agent can compete for selective binding to the soluble LGIC. For example, a sample containing the soluble LGIC can be contacted with an LGIC ligand, wherein the LGIC ligand and LGIC comprise a FRET pair, and the fluorescence emission spectrum detected, then a test agent can be added to the sample and the fluorescence emission spectrum again detected; a change in the emission spectrum indicates that the test agent has displaced (competed with) the LGIC ligand, thereby identifying the test agent as an agent that selectively binds the LGIC. Alternatively, where a LGIC and LGIC ligand comprising a FRET pair are utilized, a first sample containing the LGIC and LGIC ligand can be prepared as a control, and the LGIC ligand and test agent can be added simultaneously to a second (or other) sample, wherein the fluorescence emission spectrum of the second sample is compared with that of the first sample, and wherein a change in fluorescence emission between the samples indicates that the test agent can compete with the LGIC ligand binding and selectively bind the LGIC. As such, it should be recognized that other order of addition assays also can be performed, including, for example, assays in which the test agent is added prior to the LGIC ligand; assays in which the LGIC and test agent comprise a FRET pair and the LGIC ligand does not comprise a fluorescent moiety; and assays in which the LGIC ligand and test agent each comprise a different fluorescent moiety that comprises a FRET pair with the LGIC, but wherein the emission spectrum of the LGIC/LGIC ligand FRET pair is different from that of the LGIC/test agent.

The present methods can further include confirming that an agent identified as selectively binding a soluble LGIC also selectively binds a membrane-bound form of the LGIC. The term "membrane-bound LGIC" is used to refer to an LGIC that is bound to a membrane via a transmembrane domain and can selectively bind an LGIC ligand. The membrane generally comprises a lipid bilayer and is exemplified by a cell membrane, particularly a eukaryotic cell membrane such as a mammalian cell membrane (e.g., a human cell membrane). The membrane can be an isolated cell membrane, or can be a cell membrane in situ, in which case this aspect of the method is performed by contacting a cell comprising the cell membrane. The cell can be any type of cell that contains a cell membrane comprising a pentameric ligand-gated ion channel, including, for example, an insect cell (e.g., a *Drosophila* cell), a fungus cell (e.g., a *Neurospora* cell), a yeast cell, a *C. elegans* cell, an amphibian cell (e.g., sea urchin), an avian cell (e.g., a chick embryo fibroblast), or a human cell (e.g., a human T lymphocyte). Further, such cells useful in a method of the invention can be cells of a cell line, which have been adapted to culture; can be cells of a primary cell culture, which can be maintained in culture for at least a short period of time; or cells that have been isolated from a living organism, for example, cells isolated from a human subject. The membrane-bound LGIC also can comprise a membrane fraction of cells that express the LGIC or cells that express the membrane-bound LGIC. The membrane bound LGIC can be endogenously (naturally) expressed by the cells providing the membrane-bound LGIC, or can be an exogenous LGIC such as an LGIC encoded by a recombinant polynucleotide introduced into a suitable host cell. The membrane also can be a synthetic membrane such as a liposome.

An agent identified using the soluble LGIC can be contacted with a membrane-bound LGIC, under conditions suitable for binding of a LGIC ligand to the membrane-bound LGIC, wherein selective binding of the agent to the membrane-bound LGIC can be detected, if present. Depending on whether the agent was identified using, for example, a soluble nAChR, a soluble GABA receptor, a soluble glycine receptor, a soluble glutamate receptor, or a soluble serotonin receptor, the membrane-bound LGIC can comprise an extracellular domain of an nAChR, a GABA receptor, a glycine receptor, a glutamate receptor, or a serotonin receptor, respectively. Where the agent was identified using an AChBP such as an *Aplysia* AChBP, which is representative of a neuronal-type nAChR, the membrane-bound LGIC can be a neuronal-type nAChR.

The present invention also provides a method for identifying an agent that selectively binds an AChBP representative of a neuronal-type nAChR, which binds α-conotoxin ImI with a dissociation constant of less than about 100 nM. As used herein, reference to an AChBP being "representative of a neuronal-type nAChR" means that the AChBP binds α-conotoxin ImI with a dissociation constant that is about the same as or less than the 220 nM dissociation constant of α-conotoxin ImI with a neuronal-type nAChR α7 subunit. For example, with respect to α-conotoxin 1 ml binding, an AChBP useful in the present methods has a Kd less than 250 nM, and generally a Kd less than about 100 nM. As such, an AChBP useful in the present methods is distinguishable, for example, from a *Lymnaea* AChBP, which binds α-conotoxin ImI with a dissociation constant of about 14,000 nM (14 µM; see Example 2).

An AChBP useful in a method of the invention can be any AChBP that has characteristics of a neuronal-type nAChR, including the requisite α-conotoxin 1 ml binding affinity. In addition to the ability to selectively bind α-conotoxin ImI with a dissociation constant of less than 250 nM, the AChBP can have other characteristics of a neuronal-type nAChR, including, for example, a low affinity for epibatidine. The affinity of binding between an AChBP and ligand such as conotoxin or epibatidine can be determined, for example, by examining the dissociation rates as disclosed herein (see Example 2; Table 4) or using other methods well known and routine in the art. An AChBP representative of a neuronal-type nAChR and exhibiting high affinity α-conotoxin ImI binding is exemplified herein by an *Aplysia* AChBP as encoded by SEQ ID NO: 1, SEQ ID NO:3, or SEQ ID NO:5 (or an oligonucleotide portion thereof that encodes a polypeptide that selectively binds an AChBP ligand), or having an amino acid sequence set forth in SEQ ID NO:2 or SEQ ID NO:4 (or an AChBP ligand binding peptide portion of said polypeptide), or can be a modified AChBP such as the *Aplysia* AChBP as set forth in SEQ ID NO:2, wherein the tyrosine residue present at position 55 is substituted with a tryptophan residue.

A method for identifying an agent that selectively binds an AChBP representative of a neuronal-type nAChR can be performed, for example, by contacting a sample comprising the AChBP with a test agent, under conditions suitable for selective binding of a ligand to an AChBP (or conditions suitable for selective binding of a ligand to a neuronal-type nAChR, which exhibits high affinity (i.e., Kd<250 nM) α-conotoxin ImI binding); and detecting selective binding of the test agent to the AChBP, thereby identifying an agent that selectively binds to the AChBP, which is representative of a neuronal-type nAChR. Selective binding of the test agent to the AChBP can be detected using any method as disclosed herein or otherwise routinely used in the art for detecting specific binding of a ligand and receptor.

In one embodiment, selective binding of a test agent to a AChBP can be identified by detecting a change in fluorescence of the sample in the presence of the test agent as compared to the fluorescence in the absence of the test agent. Similar to pentameric LGICs, as disclosed herein, an AChBP exhibits intrinsic fluorescence due to the presence of tryptophan residues in the region of the ligand binding site. As such, a change in fluorescence of the AChBP due to intrinsic fluorescence can be detected upon selective binding of a test agent. The change in fluorescence can include, for example, fluorescence quenching (i.e., a decrease in 340 m emission) or fluorescence enhancement (i.e., an increase emission at or about (i.e., within about 20 nm of) 340 nm), and can be detected using a fluorescence detector, which can contain appropriate filtration that allows passage of the desired wavelength(s).

The AChBP and the test agent also can comprise a FRET pair, wherein a change in fluorescence is measured by detecting FRET. For example, a tryptophan residue of the AChBP can be a fluorescence donor, and the test agent can comprise a fluorescence acceptor that absorbs the energy of the AChBP tryptophan. The test agent can emit at the same or different wave length such that a detectable change in fluorescence emission (e.g., a change in amplitude and/or a change in wavelength) due to selective binding of a test agent can be detected. The test agent can inherently absorb and/or emit fluorescence, or can be operatively linked to a moiety that allows the test agent to act as a member of a FRET pair (i.e., a fluorescence acceptor or fluorescence donor). Alternatively, the test agent can comprise a non-fluorescent acceptor molecule, which acts as a quencher, wherein the fluorescence emission of the AChBP increases when the quenching test agent is displaced from close proximity to the donor tryptophan molecule of the AChBP, or the fluorescence emission decreases when the quencher is brought into close proximity to the tryptophan residue due to selective binding of the test agent.

Selective binding of a test agent also can be detected using a fluorescence based competition assay format, wherein the test agent and a AChBP ligand compete for selective binding to the AChBP. The AChBP ligand can be a ligand that enhances or quenches AChBP fluorescence upon selective binding. Upon selective binding of a test agent, an AChBP ligand is displaced from the AChBP or binding is disrupted and the enhanced or quenched fluorescence due to ligand binding to the AChBP is not observed. As discussed above, the AChBP ligand can be gallamine, which binds to the AChBP and enhances fluorescence of the AChBP, wherein selective binding of the test agent results in fluorescence quenching; or the AChBP ligand and the AChBP can comprise a FRET pair, wherein selective binding of a test agent to the AChBP alters the proximity of the donor and acceptor molecules, thereby producing a change in fluorescence upon selective binding of the test agent compared to the fluorescence emission in the absence of the test agent.

Selective binding of a test agent to the AChBP also can be detected using a scintillation proximity assay (SPA; Amersham Biosciences; Piscataway N.J.). In using SPA to detect selective binding of a test agent to an AChBP, the test agent can comprise a radiolabel, and the AChBP is bound to a solid support comprising a scintillant, wherein, upon selective binding to the AChBP, the radiolabel causes scintillation of the scintillant. As such, detecting scintillation of the sample is indicative of selective binding of the test agent to the AChBP. SPA also can be performed using a test agent (or plurality of test agents) linked to a solid support comprising a scintillant (e.g., an addressable array of test agents on a support such as a silicon wafer comprising scintillant), and the AChBP can be radiolabeled, wherein the site(s) of scintillation identifies a test agent (or test agents) that selectively bind the AChBP.

SPA technology generally uses a support system (e.g., a bead) in which scintillant is trapped or impregnated. The support system can further comprises high affinity receptor molecules immobilized on or near its surface such that the receptors are accessible to suitable ligands. Scintillation occurs when a weak energy radioactive isotope (e.g., tritium) is brought sufficiently close to the SPA support system due, for example, to selective binding of a radiolabeled ligand. Scintillation can be measured directly, without a need for separation of unbound radiolabeled molecules (e.g., test agents or ligands) from bound radiolabeled molecules. As such, SPA based assays do not require cumbersome washing steps, and conveniently can be performed in a high throughput screening format.

The SPA support system can be a bead that is impregnated with scintillant and to which an AChBP (or soluble pentameric LGIC) is operatively linked. Such beads are commercially available (e.g., Amersham Biosciences), or can be prepared using routine methods. Alternatively, scintillant can be incorporated onto a surface such as onto wells of a microtiter plate, depressions in a chip, or positions on a slide; or into a fiber. As such, the support system can be composed of any material capable of trapping the scintillant, and can have any appropriate shape, configuration or composition provided that the operatively linked LGICs and/or AChBPs maintain a conformation suitable for selective binding of a ligand and that the selective binding of a radiolabeled ligand (or test agent) results in sufficient proximity for scintillation of the scintillant.

Selective binding of a test agent to an AChBP also can be detected using other well known and routine methods including, for example, equilibrium dialysis, surface plasmon resonance, and the like. A test agent or ligand that selectively binds an AChBP also can be identified using methods of molecular modeling. Modeling systems useful for the purposes disclosed herein can be based on structural information obtained, for example, by crystallographic analysis or nuclear magnetic resonance analysis, or on primary sequence information (see, for example, Dunbrack et al., "Meeting review: the Second meeting on the Critical Assessment of Techniques for Protein Structure Prediction (CASP2) (Asilomar, Calif., Dec. 13-16, 1996). *Fold Des.* 2(2): R2742, (1997); Fischer and Eisenberg, *Protein Sci.* 5: 947-55, 1996; (see, also, U.S. Pat. No. 5,436,850); Havel, *Prog. Biophys. Mol. Biol.* 56: 43-78, 1991; Lichtarge et al., *J. Mol. Biol.* 274: 325-37, 1997; Matsumoto et al., *J. Biol. Chem.* 270: 19524-31, 1995; Sali et al., *J. Biol. Chem.* 268: 9023-34, 1993; Sali, *Molec. Med. Today* 1: 270-7, 1995a; Sali, Curr. Opin. Biotechnol. 6: 437-51, 1995b; Sali et al., *Proteins* 23: 318-26, 1995c; Sali, *Nature Struct. Biol.* 5: 1029-1032, 1998; U.S. Pat. Nos. 5,933,819; 5,265,030, each of which is incorporated herein by reference).

The crystal structure coordinates of an AChBP (e.g., *Aplysia* AChBP as set forth in SEQ ID NO:2) can be used to design compounds that bind to the protein and alter its physical or physiological properties in a variety of ways. The structure coordinates of the AChBP can be used, for example, to computationally screen small molecule data bases for agents that bind to the polypeptide to develop modulating or binding agents, which can act as agonists or antagonists of LGIC activity. Such agents can be identified by computer fitting kinetic data using standard equations (see, for example, Segel, "Enzyme Kinetics" (Wiley & Sons 1975), which is incorporated herein by reference).

Methods of using crystal structure data to design inhibitors or binding agents are known in the art. For example, AChBP (or pentameric LGIC) coordinates can be superimposed onto other available coordinates of similar receptors, including receptors having a bound inhibitor, to provide an approximation of the way the inhibitor interacts with the receptor. Computer programs employed in the practice of rational drug design also can be used to identify compounds that reproduce interaction characteristics similar to those found, for example, between a neuronal-type nAChR and a ligand such as conotoxin. Detailed knowledge of the nature of the specific interactions allows for the modification of compounds to alter or improve solubility, pharmacokinetics, and the like, without affecting binding activity.

Computer programs for carrying out the activities necessary to design agents using crystal structure information are well known. Examples of such programs include, Catalyst Databases™—an information retrieval program accessing chemical databases such as BioByte Master File, Derwent WDI and ACD; Catalyst/(HYPO™—generates models of compounds and hypotheses to explain variations of activity with the structure of drug candidates; Ludi™—fits molecules into the active site of a protein by identifying and matching complementary polar and hydrophobic groups; and Leapfrog™—"grows" new ligands using a genetic algorithm with parameters under the control of the user.

Upon identifying an agent that selectively binds an AChBP representative of a neuronal-type nAChR having high affinity conotoxin ImI binding, the agent can be further examined for selective binding to a neuronal-type nAChR (e.g., a human neuronal-type nAChR). Methods for detecting selective binding of an agent to a neuronal-type nAChR can be performed as disclosed herein, including, for example, contacting a neuronal-type nAChR with the agent under conditions suitable for binding of an nAChR ligand to the neuronal-type nAChR, and detecting selective binding of the agent to the nAChR, thereby identifying a neuronal-type nAChR ligand. The neuronal-type nAChR can be a soluble nAChR, such as the extracellular domain of an nAChR, or a membrane-bound nAChR.

An advantage of the present methods is that they can be adapted to high throughput analysis and, therefore, can be used to screen combinatorial libraries of test agents in order to identify those agents that can selectively bind to an LGIC. Methods for preparing a combinatorial library of molecules that can be tested for a desired activity are well known in the art and include, for example, methods of making a phage display library of peptides, which can be constrained peptides (see, for example, U.S. Pat. Nos. 5,622,699; 5,206,347; Scott and Smith, *Science* 249: 386-390, 1992; Markland et al., *Gene* 109: 13-19, 1991; each of which is incorporated herein by reference); a peptide library (U.S. Pat. No. 5,264,563, which is incorporated herein by reference); a peptidomimetic library (Blondelle et al., *Trends Anal. Chem.* 14: 83-92, 1995; a nucleic acid library (O'Connell et al., *Proc. Natl. Acad. Sci., USA* 93: 5883-5887, 1996; Tuerk and Gold, *Science* 249: 505-510, 1990; Gold et al., *Ann. Rev. Biochem.* 64: 763-797, 1995; each of which is incorporated herein by reference); an oligosaccharide library (York et al., *Carb. Res.*, 285: 99-128, 1996; Liang et al., *Science*, 274: 1520-1522, 1996; Ding et al., *Adv. Expt. Med. Biol.* 376: 261-269, 1995; each of which is incorporated herein by reference); a lipoprotein library (de Kruif et al., *FEBS Lett.* 399: 232-236, 1996, which is incorporated herein by reference); a glycoprotein or glycolipid library (Karaoglu et al., *J. Cell Biol.* 130: 567-577, 1995, which is incorporated herein by reference); or a chemical library containing, for example, drugs or other pharmaceutical agents (Gordon et al., *J. Med. Chem.* 37: 1385-1401, 1994; Ecker and Crooke, *BioTechnology* 13: 351-360, 1995; each of which is incorporated herein by reference). Polynucleotides can be particularly useful as agents that can modulate a specific interaction of an agent or ligand and an LGIC because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

In performing an assay of the invention in a high throughput format, soluble LGICs or membrane-bound LGICs, including, for example, isolated cell membranes or intact cells, can be used. An advantage of using intact cells is that the method can identify an agent that selectively binds an LGIC in particular cells or cell types. For example, a plurality of cells from a subject can be arranged in an array, which can be an addressable array, on a solid support such as a microchip, on a glass slide, on a bead, or in a well, and the cells can be contacted with different agents, which were identified as selectively binding to an LGIC according to the methods of o the invention, to identify one or more agents having desirable characteristics, including, for example, minimal or no toxicity to the cell, desirable cellular uptake characteristics, and the like. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays.

A plurality of test agents (e.g., a combinatorial library of test agents) can examined for selective binding to a soluble LGIC in a high throughput format as disclosed herein. One or more test agents also can be examined for selective binding to at least two different LGICs (e.g., a muscle-type nAChR and a neuronal-type nAChR; or a nAChR and a GABA receptor). Advantages of performing the present methods in a high throughput format include, for example, that duplicates, triplicates, or more of an assay can be performed, whereby statistically significant results can be obtained; and that one or more (positive and/or negative) controls can be performed in parallel, thus providing a means to obtain standardized results (e.g., among samples performed at different times or under different conditions).

The present invention also provides a polynucleotide as set forth in SEQ ID NO:5, which encodes an *Aplysia* AChBP as set forth in SEQ ID NO:2. The polynucleotide of the invention comprises a mammalian codon biased polynucleotide that encodes an AChBP lacking the naturally occurring leader sequence. As such, a polynucleotide of the invention provides the advantage that it encodes an AChBP that is readily expressible in mammalian host cells. Accordingly, the invention also provides a vector containing the polynucleotide, and host cells that contain the polynucleotide and/or the vector containing the polynucleotide.

A polynucleotide of the invention can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes a peptide, for expressing the encoded peptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, *baculovirus*, retrovirus, *lentivirus, adenovirus*, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther:* 1: 51-64,1994; Flotte, *J. Bioenerg. Biomemb.* 25: 37-42, 1993; Kirshenbaum et al., *J. Clin. Invest.* 92: 381-387, 1993; each of which is incorporated herein by reference).

A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

The present invention further provides kits useful for practicing a method of identifying an agent that selectively binds an AChBP and/or an LGIC. A kit of the invention can contain, for example, at least one soluble LGIC that fluoresces, or at least one AChBP that fluoresces; and can further contain at least one LGIC ligand. In one aspect of such a kit, the LGIC ligand comprises a fluorescent moiety, wherein the soluble LGIC and LGIC ligand comprise a FRET pair. In another aspect, the AChBP ligand comprises a fluorescent moiety, wherein the AChBP and AChBP ligand comprise a FRET pair.

A kit of the invention also can contain a plurality of soluble LGICs and/or AChBPs, which can be present in the kit in a free form (i.e., isolated from products with which it otherwise may be associated with in a cell in nature), or can be associated with (e.g., operatively linked to) a support. For example, a plurality of soluble LGICs and/or AChBPs can be contained in a multi-well plate (e.g., a 96 well or 384 well plate), or can be coupled to a glass slide or a silicon wafer, and can be arranged in an array (e.g., an addressable array). Such compositions, wherein LGICs and/or AChBPs of the plurality are the same or different, conveniently can be used in high throughput format type assays.

A kit of the invention can additionally contain a container means. The container means may be any suitable container, but will typically be a glass vial or jar, a plastic pack, etc. In one embodiment, the container means may be a foil or plastic pouch which contains LGIC and/or AChBP, which can be immobilized on a solid support (see above). The kit also can contain reagents such as buffers or diluents, and/or sample handling means such as pipettes, reaction vials, vessels, tubes, or filters, which can be useful for practicing a method of the invention. In addition, the kit can contain written or electronic instructions, which can set forth suitable conditions for carrying out the present methods (e.g., reaction conditions, mixing ratios, amounts, incubation times, and/or criteria for evaluating results).

The following examples are intended to illustrate but not limit the invention.

EXAMPLE 1

Ligand Binding to an Acetylcholine Binding Protein is Detectable by Monitoring Tryptophan Fluorescence This Example demonstrates that ligand binding to an AChBP results in detectable changes in tryptophan fluorescence by the AChBP.

The characterization of an AChBP from the fresh water snail, *Lymnaea stagnalis*, showed it to be a structural homolog of the extracellular domain of nAChRs. To ascertain whether the AChBP exhibits the recognition properties and functional states of an nAChR, the protein was expressed in milligram quantities from a synthetic cDNA transfected into human embryonic kidney (HEK) cells. The protein secreted into the medium showed a pentameric rosette structure with ligand stoichiometry approximating five sites per pentamer. Binding of acetylcholine, selective agonists, and antagonists ranging from small alkaloids to larger peptides results in substantial quenching of the intrinsic tryptophan fluorescence. Using stopped-flow techniques, rapid rates of association and dissociation of agonists and slow rates for the α-neurotoxins were demonstrated. Since agonist binding occurs in millisecond time frames, and the α-neurotoxins may induce a distinct conformational state for the AChBP-toxin complex, the snail protein showed many of the properties expected for receptor recognition of interacting ligands. Thus, the marked tryptophan quenching not only illustrates the importance of aromatic residues in ligand recognition, but establishes that the AChBP will be a useful functional as well as structural surrogate of the nicotinic receptor.

Gene Synthesis and Protein Expression—Seven double-stranded oligonucleotides between 80 and 126 bp reflecting codon usage in mammalian cells and containing appropriate overhangs for ligation were synthesized (6). The oligonucleotides were assembled into three ligation products, which were inserted into construction vectors and sequenced by automated sequencing. After digestion with appropriate restriction enzymes followed by band isolation, the inserts were ligated into a p3×FLAG-CMV-9 expression vector (Sigma) containing a preprotrypsin leader peptide followed by a N-terminal 3×FLAG epitope (2). The expression plasmid also contained neomycin acetyltransferase for clonal selection. Transfection of the plasmid into human embryonic kidney cells produced an epitope-attached glycoprotein secreted primarily into the medium. Selection with G418 yielded a stable cell line secreting AChBP. Ultraculture medium (Bio Whittaker) was collected at 3-day intervals from multitier flasks for several weeks. Adsorption onto a FLAG antibody column followed by elution with the 3×FLAG peptide yielded purified protein in quantities between 1 and 2.5 mg/liter.

Fluorescence Assays—Fluorescence measurements were performed on a Jobin Yvon-Spex Fluoromax 2 fluorometer (Instruments S. A., Inc., Edison, N.J.). AChBP was excited at 280 nm and emission intensity monitored for 0.1 second intervals at unitary wavelengths between 337 and 343 nm.

Stopped-flow Kinetics—Stopped-flow measurements were obtained using an Applied Photophysics SX.18MV (Leatherhead, UK) stopped-flow spectrofluorometer. Excitation was at 280 nm, and a cut-off filter at 305 nm was used to collect the fluorescence signal. Measurements of binding of the dansyl choline analogues employed 280 nm excitation and measured the enhanced fluorescence using a 420-nm cut-off filter. Rates of association and dissociation were estimated from the slope and ordinate intercept of plots of overall rate of fluorescence change versus ligand concentration. Dissociation rates were also estimated in several cases by reacting the preformed complex with a large excess of gallamine in the stopped-flow instrument and observing the time course of the increase in fluorescence.

Purification of AChBP secreted into the medium produced a single band on SDS gels migrating at ~35 kDa (data not shown). Treatment with PNGase to remove N-linked oligosaccharides enhances the migration rate considerably. N-terminal sequencing and matrix-assisted laser desorption ionization mass spectrometry after deglycosylation yielded a sequence and mass consistent with cleavage of the leader peptide. Negative staining electron microscopy showed typical rosette structures expected of a pentameric subunit assembly. Hydrodynamic analysis revealed a Stokes radius of 57 Å from gel filtration and a sedimentation coefficient of 4.9 S from sucrose density gradients; values were also consistent with pentamer formation.

Stoichiometry of ligand binding was estimated from AChBP tryptophan quenching through titration by high affinity ligands (FIG. 1). In separate preparations, this yielded values of 4.7-5.6 mol/mol of pentamer or 0.94 to 1.1 mol/mol of 26,551 dalton subunit based on quantitative amino acid analysis. These data show, with epibatidine as a high affinity ligand, about 50% quenching of the intrinsic tryptophan fluorescence, a typical quenching value for most of the quaternary and tertiary amines used in this study. Since these ligands, with the exception of the dansyl choline derivatives, lack the spectral overlap with tryptophan emission necessary for fluorescence resonance energy transfer (FRET) (7), the precise mechanism of quenching is unknown. However, at least two (Trp-53 and Trp-143) and perhaps a third (Trp-82) of the five tryptophans are found in proximity to the bound ligand (*Lymnaea* number) (3). The organic cation in fitting into this aromatic nest of tryptophans and tyrosines may disrupt aromatic connectivity established between the side chains (8).

Upon binding of ligands lacking the capacity for FRET, tryptophan fluorescence quenching has also been observed for acetylcholinesterase (9); its binding site is at the base of a narrow gorge whose base and walls are lined with aromatic residues (10). In the muscle and α7 nAChR, residue substitution of tryptophans homologous to residues 53 and 143 of the *Lymnaea* species reduces ligand affinity, but does not eliminate binding (11, 12), and a charge-transfer complex involving one or more tryptophans has been proposed to stabilize various ligand complexes (13, 14). Systematic substitution of other aromatic residues for the five tryptophans should enable one to delineate further their individual contributions to quenching of fluorescence.

FIG. 1 illustrates equilibrium titration of *Lymnaea* AChBP with α-bungarotoxin and epibatidine. AChBP at 300 nM was titrated in a 4×4-mm cuvette with incremental quantities of the peptide antagonist and the alkaloid agonist. Since quenching by α-bungarotoxin is only 15-20% of the unliganded receptor fluorescence, a receptor-gallamine complex was formed by addition of 2 μM gallamine to enhance fluorescence prior to the α-bungarotoxin addition. The contribution of the fluorescence from the added α-bungarotoxin was subtracted from the titration curve. The single tryptophan in α-bungarotoxin has less than 2% of the emission intensity at 335 nm of the tryptophans in the receptor-gallamine complex, so only a small correction is necessary. Fluorescence was recorded in a SPEX Fluoromax2 spectrofluorometer at 25° C. Protein content was determined by quantitative amino acid analysis with α subunit molecular weight of 26,551 daltons. Fluorescence excitation was at 280 mm; emission maxima were measured over the range of 337-343 nm.

Figures 2A, 2B, 2C, 2D:
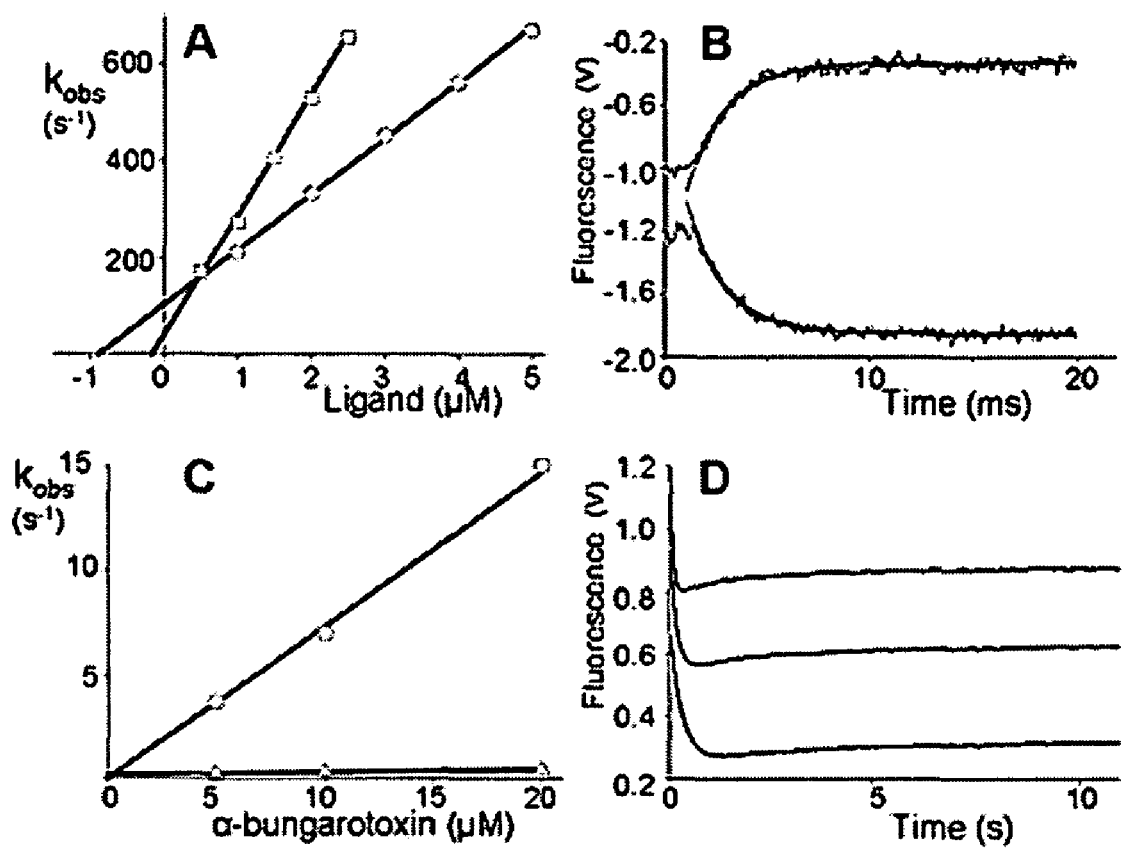
FIGS. 2A to 2D illustrate kinetics of ligand association with AChBP.

Stopped-flow kinetic studies of ligand association are shown in FIG. 2. Data for several ligands, monitored by *Lymnaea* AChBP fluorescence quenching, are tabulated in Table 1. Rates of association and dissociation approach the time resolution of the stopped-flow technique (~1 ms). A comparison of agonists shows that the bimolecular rates of agonist binding approach the diffusion limitation and the rate constants found in single channel or voltage-current relaxation analyses for the muscle or neuronal nicotinic receptor (15-20). Rates of dissociation are slower than dissociation of ligand from the activatible receptor, but of nearly the same magnitude as dissociation from the open channel state, and more rapid than dissociation from the presumed desensitized state (15-20). Hence, agonists bind and dissociate with rates expected from electrophysiologic studies for an open channel state of the receptor. In fact, certain residues in the transmembrane span of the receptor have been shown to enhance dissociation of ligands from the activatible, closed channel state of the receptor (21). Moreover, the AChBP structure may resemble more closely the open channel conformation of the Torpedo acetylcholine receptor (22).

Table 1, below, illustrates *Lymnaea* AChBP ligand binding kinetics. $k_1$ and $k_{-1}$ were determined from rate measurements at various ligand concentrations according to $k_{obs}=k_1(L)+k_{-1}$ (cf. FIG. 2) and $K_d$ was calculated from $k_{-1}/k_1$. S.E. values reflect values from three or more measurements. Where S.E. values are not shown, values reflect an average of two measurements.

TABLE 1

| Ligand | $k_1$ $\times 10^8$ $M^{-1}$ $s^{-1}$ | $k_{-1}$ $s^{-1}$ | $K_d$ nM |
|---|---|---|---|
| Decamethonium | 3.2 ± 0.17 | 120 ± 17 | 380 |
| Dansyl-C$_2$-choline[a] | 2.1 | 2.9 | 14 |
| Gallamine | 2.5 ± 0.14 | 36 ± 6.5 | 140 |
| d-Tubocurarine | 2.0 | 30 | 150 |
| (+)-Epibatidine | 1.7 ± 0.26 | 0.027 ± 0.037 | 0.16 |
| (−)-Nicotine | 1.5 | 5.7 | 38 |
| Dansyl-C$_6$-choline[b] | 1.3 | 7.6 | 58 |
| Acetylcholine | 1.1 ± 0.12 | 120 ± 16 | 1000 |
| Waglerin-1 | 0.048 | 31 | 6500 |
| α-Cobratoxin | 0.033 | 0.011 | 3.2 |
| α-Bungarotoxin | 0.0097 ± 0.002 | 0.0017 ± 0.0003 | 1.8 |

[a]5-Dimethylaminonaphthylsulfonamidoethyltrimethylammonium.
[b]5-Dimethylaminonaphthylsulfonamidohexyltrimethylammonium Given the proposed role for AChBP in scavenging the neurotransmitter in synapses (4), an association rate for acetylcholine similar to that found for the receptor would be expected to achieve efficient function. Also, the kinetic constants for the antagonist, d-tubocurarine, are of comparable magnitude with those found electrophysiologically for the receptor (23). No evidence for appreciable cooperativity of binding was found in the kinetic profiles.

Epibatidine and α-bungarotoxin have equilibrium dissociation constants for *Lymnaea* AChBP that differ by only an order of magnitude, yet the rate of association for the peptide antagonist is ~200-fold slower than for the nicotinic agonist (Table 1). If the association reactions for α-bungarotoxin are run at higher concentrations, two steps in the reaction are evident with the rapid step being bimolecular- and concentration-dependent. The unimolecular step ($k_2$=0.34 $s^{-1}$) shows a small enhancement in fluorescence that diminishes, but does not eliminate, the overall fluorescence quenching. The slower α-neurotoxin kinetics of association, which also has been documented in nicotinic receptors from several species (24-26), and the linked unimolecular step seen here are suggestive of the α-bungarotoxin locking the *Lymnaea* AChBP into a distinctive conformational state. The single tryptophan in α-bungarotoxin has ~2% of the fluorescence intensity of the five tryptophans in each AChBP subunit. The fluorescence change in the slow step could emerge from enhanced fluorescence of the single tryptophan of the toxin in the complex or a slight enhancement of the AChBP tryptophans after formation of the initial complex. Irrespective of the tryptophans contributing to the signal differences, the slower unimolecular isomerization points to differing positions of the tryptophans in the initial complex and the final equilibrium state.

The tris-quaternary antagonist, gallamine, when associated with the receptor, results in an enhancement of the tryptophan fluorescence, suggesting that the stabilization of this ligand may differ from the other agonists and antagonists studied. The three triethylammonioethyl groups that emanate from the pyrogallol ring probably preclude full insertion of the ring into the aromatic pocket. Rather stabilization involving the quaternary ammonium ligands and anionic moieties at the subunit interface account for the different binding orientation of gallamine, resulting in fluorescence enhancement (data not shown). Since gallamine binding appears mutually exclusive with the other agonists and antagonists listed in Table 1, reaction of the various ligand-AChBP complexes with gallamine by stopped-flow provided a valuable means of confirming the dissociation rates of the various antagonists (Table 1), as well as measuring the stoichiometry of ligand binding for ligands that quench to a lesser extent than epibatidine (FIG. 1).

Quite apart from establishing ligand specificity for the AChBP, intrinsic tryptophan fluorescence quenching affords a universal means of directly following ligand binding to the AChBP without the necessity of developing competition studies with radioactive or fluorescent ligands. Substitution of sequences unique to particular receptor subtypes may allow one to examine selectivity of various AChBP-receptor chimeric sequences fashioned after the neuronal or muscle subtypes of receptor. The ligand binding kinetics seen with the AChBP reveals similarities to kinetics anticipated for ligand binding to the many subtypes of nicotinic receptor. Physical measurements in solution should enable one to correlate conformation with kinetic parameters of ligand recognition, and add another dimension to investigating specificity of this unique binding protein in relation to the larger family of receptor-related offspring.

EXAMPLE 2

Structural and Ligand Recognition Characteristics of *Aplysia* Acetylcholine Binding Protein This Example describes the generation of an AChBP from *Aplysia californica* by synthesis of a cDNA present in a database, and expression of the AChBP in mammalian cells in culture.

Secreted *Lymnaea* and *Aplysia* AChBPs were purified by elution from columns of attached antibodies directed to the FLAG epitope encoded in the expression construct. Although the sequences of the two proteins from marine and fresh water mollusks exhibit the characteristic features of the extracellular domain of the nicotinic receptor, they only possess 33% amino acid identity. Both assemble as stable pentamers with five binding sites per pentamer, yet they show distinguishing features of stability and sensitivity to epitope tag placement. Both proteins exhibit changes in tryptophan fluorescence upon ligand binding, however the magnitude of the changes differs greatly. Moreover, certain ligands showed marked differences in dissociation constants for the two proteins and can be regarded as distinguishing or signature ligands. Hence, the two soluble proteins from mollusks, which can be studied by a variety of physical methods, become discrete surrogate proteins for the extracellular domains of distinct subtypes of nicotinic acetylcholine receptors.

Construction of an Expression Vector cDNA—The cDNA encoding the *Aplysia* AChBP (A-AChBP) was synthesized using the nucleotide coding sequence found in an *Aplysia* database. Briefly, oligonucleotides extending up to 100 bp and containing triplet codons with frequent mammalian codon usage (35) were ligated into a p3×FLAG-CMV-9 expression vector (Sigma) containing a preprotrypsin leader peptide followed by an N-terminal 3×FLAG epitope and a C-terminal six-histidine (His) tag. Three alternative expression plasmids were synthesized and compared to the corresponding plasmids from the *Lymnaea* sequence. One had an N-terminal 3×FLAG but was devoid the C-terminal (His) tag. The two others contained a 1×FLAG tag on the C-terminus or N-terminus. Restriction sites were also engineered into the coding sequence at convenient locations to allow for formation of removable cassettes for subsequent mutagenesis studies.

Conditions for protein expression paralleled that of the *Lymnaea* AChBP (34). Briefly, HEK cells were transfected with A-AChBP cDNA along with a companion neomycin acetyltransferase gene and selected for stable expression using G418. Media containing the secreted A-AChBP was collected at 2 to 3 day intervals and cells replenished with fresh media. Collected media was preserved prior to purification with 0.02% NaN$_3$. A-AChBPs were purified by adsorption onto a flag antibody column followed by elution with the 3×FLAG peptide.

Fast Protein Liquid Chromatography—Gel filtration was carried out using a Pharmacia LCC 500 plus FPLC with a Superdex 200 gel filtration column. Fifty μl of A-AChBP protein at 100 μg/ml protein concentration in Tris HCl buffered saline (TBS) (20 mM Tris HCl, 150 mM NaCl, pH 7.4)+0.02% azide was loaded on the column at a rate of 0.5 mL/min. Protein in the eluent was monitored by absorption at 280 nm.

Sedimentation equilibrium analysis—Analytical ultracentrifugation was conducted in a Beckman/Coulter XL-I centrifuge equipped with UV absorption optics using a 60 Ti rotor. Protein solutions of 100 μg/ml were used in a six-channel charcoal-filled epon centerpiece loaded with 110 μl of sample and 125 μl of reference buffer (20 mM Tris HCl, 150 mM NaCl, pH 7.4). Individual samples were centrifuged at 20° C. for 16 hours at 10,000 and 12,000 rpm. Equilibrium was attained as judged by overlay of the last three sequential scans. Data were recorded in step mode with a Δr of 0.001 cm, and five replicate absorption measurements were performed at each step every two hours. A partial specific volume, $\bar{\upsilon}$=0.71, for AChBPs was calculated using Sedntrep software (version 1.06) accounting for total sugar composition. Molar masses of the proteins were calculated using XL-A/XL-I Data Analysis Software version 4.0 based on Origin™ program.

Estimation of Binding Parameters from Fluorescence Signal—Equilibrium fluorescence was monitored using a Tecan Safire fluorescence plate reader in 96 well UV plates (Costar, USA). AChBP was excited at 280 nm and emission intensity monitored at 340 nm using an excitation and emission slit widths of 7.5 nm in a bottom read mode at room temperature. AChBP, 50-100 nM in binding site concentration, was equilibrated with half log dilutions of ligand. Data were normalized, and $K_i$'s were calculated by fitting to a sigmoidal dose-response curve with variable slope in Prism GraphPad 3.0. Y=Min+(Max−Min)/(1+10^((LogEC$_{50}$−X)*HillSlope)); where X is the log of concentration. Y is the fractional binding. $K_i$ is calculated from $Y_{50}/(1+((ligand)/K_d))$.

To determine ligand stoichiometries, AChBP at 400 nM-650 nM in binding sites, estimated from protein concentration, was titrated with sequentially increasing concentrations of epibatidine or methyllycaconitine. The concentration of binding sites greatly exceeded the $K_d$ of the ligand. Accordingly, quenching was essentially linear with concentration until the binding sites were saturated and no further quenching was apparent.

pH Stability of AChBPs—AChBP at a concentration of 0.5 nM binding sites was mixed with 0.1 mg/ml of beads for the PVT copper His-Tag scintillation proximity assay, according to manufacturer's recommendations (Amersham Bioscience, USA). The beads were suspended in 0.01M phosphate/pyrophosphate buffers between pH 5.0 and 11. ($^3$H)-epibatidine at 20 nM was added to the 200 uL reaction and allowed to equilibrate at room temperature at the respective pH for 1 hr or the designated time and then read on a Beckman LS 6500 scintillation counter.

Stopped-flow Kinetics—Stopped-flow measurements were obtained using an Applied Photophysics SX.18MV (Leatherhead, UK) stopped-flow spectrofluorometer. AChBP was excited at 280 nm and emission was monitored above 305 nm using a cut off filter. Changes in fluorescence emission intensity were fit to a first order equation and resulting rates plotted versus ligand concentration. Association and dissociation were estimated from the slope and ordinate intercept. In addition, dissociation rate constants were estimated by monitoring the dissociation of the ligand-AChBP complex by addition of excess gallamine and following the increase in fluorescence. Sufficient gallamine was used to ensure that the rate was limited by the dissociating ligand rather than the scavenging of free ligand by gallamine.

Expression of the Acetylcholine Binding Protein from the Synthesized Oligonucleotide—Using the published sequence of AChBP from *Lymnaea stagnalis*, a BLAST search of the Entrez pub med protein database yielded a sequence from *Aplysia* californica (A-AChBP) that shared 33% amino acid identity with *Lymnaea*. The A-AChBP contained internal sequence features suggesting it was a soluble binding protein rather than a truncated receptor sequence. Given that *Aplysia* and *Lymnaea* are evolutionarily distant mollusks, the A-AChBP was examined to determine whether it was an ortholog with distinct pharmacological properties.

FIG. 3 shows an alignment of soluble binding proteins with the N-terminal domains of transmembrane spanning heteromeric $(\alpha 1)_2\beta\gamma\delta$ nicotinic receptor in muscle and the homomeric α7 neuronal receptor. A-AChBP lacks a transmembrane spanning region. Furthermore, the cysteine loop region between residues 127 and 140 (*Aplysia* numbering), is highly conserved among binding proteins, but distinct from that of nAChR's, where it is also highly conserved among the receptor molecules. This region is thought to interact and link with the transmembrane domain of the receptor (22,36), but reveals a hydrophilic surface in the case of the binding proteins.

HEK 293 cells, transfected with the A-AChBP gene and selected as stable transfectants, secreted the encoded protein into the media. Typically, 1 to 3 mg of A-AChBP was purified from a liter of media. A cDNA encoding the A-AChBP, isolated from a sensory cell *Aplysia* library, when placed in a viral expression vector, did not express active secreted protein. When sequenced, the cloned A-AChBP differed by valine being substituted for alanine at residues 43 and 138. A sequence with the two valine residue substitutions was not found in the *Aplysia* database.

Characterization of the Binding Protein—Due to variable aggregation of initial preparations of A-AChBP, we investigated the role played by a C-terminal 6×His tag and several FLAG tags of variable length at both the N- and C-termini of the AChBP coding sequence. Table 2 shows the typical expression achieved after purification for four constructs for both *Lymnaea* and *Aplysia* genes. Purified protein for each construct was analyzed by SDS-PAGE and gel filtration. A 6× histidine tag on the C-terminus resulted in extensive aggregation or oligomerization in the *Aplysia* cDNA following purification. The aggregation varied from a small shoulder slightly larger than the pentameric 190 kDa to an aggregate peak in the void volume upon gel filtration. The presence of the larger oligomers accumulated rapidly at room temperature and 4° C. By contrast, the *Lymnaea* protein showed minimal aggregation initially, but formed higher order oligomers over a period of several months when stored at 4° C. Expression from constructs encoding the *Lymnaea* AChBP or the *Aplysia* AChBP, without the 6×-His tag, yielded minimal aggregation over several months. Both eluted at an apparent molecular weight of about 190,000 daltons.

Table 2 shows properties of the acetylcholine binding proteins from *Lymnaea* and *Aplysia*. Summarized are the constructs with their corresponding purification tag, molecular weight, expression and physical properties. Molecular weights designate calculated values for the mature peptide only. Large additional peaks at heavier apparent molecular weights, as observed by gel filtration, were interpreted as aggregation. A positive indication (+) for oligosaccharide indicates extensive glycosylation processing with multiple bands; all forms contain N-linked oligosaccharides. Expression is shown as a range from several preparations and was quantified as mg of protein purified to apparent homogeneity per liter of harvested media.

TABLE 2

| Construct | Peptide MW (Lymnaea) | Peptide MW (Aplysia) | Location of Purification Tags | Aggregation Aplysia | Aggregation Lymnaea | Oligosaccharide | Yield (mg/L) |
|---|---|---|---|---|---|---|---|
| I | 27,586 | 28,941 | 3xN-FLAG/C-6xHis | + | +/− | + | 2-3 |
| II | 26,551 | 27,905 | 3xN-FLAG | − | − | + | 2-3 |
| III | 24,834 | 26,074 | 1xC-FLAG | − | − | − | 0.5-1 |
| IV | 24,834 | 26,187 | 1xN-FLAG | − | − | + | 3-4 |

Constructs modified at the N-terminus showed variable glycosylation evident in the multiple bands on SDS-PAGE. Only the construct with a single C-terminal FLAG tag (III) migrated as a single, but broad band. Its expression yield, however, was lower than those of the N-terminally tagged constructs (Table 2). Neither initial aggregation nor heavy glycosylation were observed to influence ligand-binding parameters, although the aggregated proteins were not studied in detail. Analytical ultracentrifugation yielded profiles that fit to a molecular weight estimate of 155,100±1,400 daltons for A-AChBP and 151,700±800 daltons for L-AChBP; these are the values expected for a glycosylated pentamer.

Figure 4:
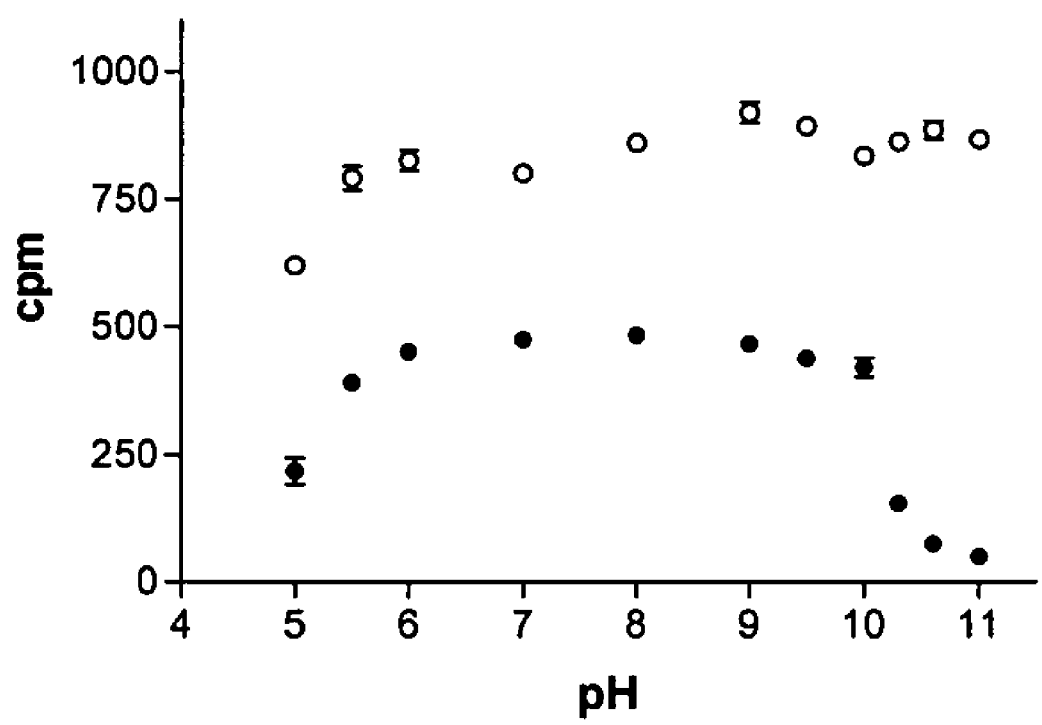
FIG. 4 illustrates pH stability of the AChBP. Samples of 0.5 nM AChBP binding sites was incubated with 20 nM ($^3$H)-epibatidine for 1 hour and monitored using a scintillation proximity assay. The pH was varied between 5.0 and 11 using a 100 mM phosphate/pyrophosphate buffer. Open symbols denote *Lymnaea* AChBP data and closed symbols denote *Aplysia* AChBP data. Standard deviation indicated for some points.

Protein stability was examined in 0.01M phosphate/pyrophosphate buffer between pH 5.0 and 11 (FIG. 4). In addition, solutions were kept at room temperature in the dark and stability monitored over a month. ($^3$H)-epibatidine sites were not lost during the 1 hr incubation for L-AChBP between pH 5.5 and pH 11, whereas A-AChBP rapidly lost activity above pH10. Above pH 8, L-AChBP was stable for 6 days, but showed some loss of signal after about one month. A-AChBP showed little binding above pH 8.0 after 6 days, but was completely stable between pH 6.0 and 7.0 for the observed period.

Figures 6A, 6B:
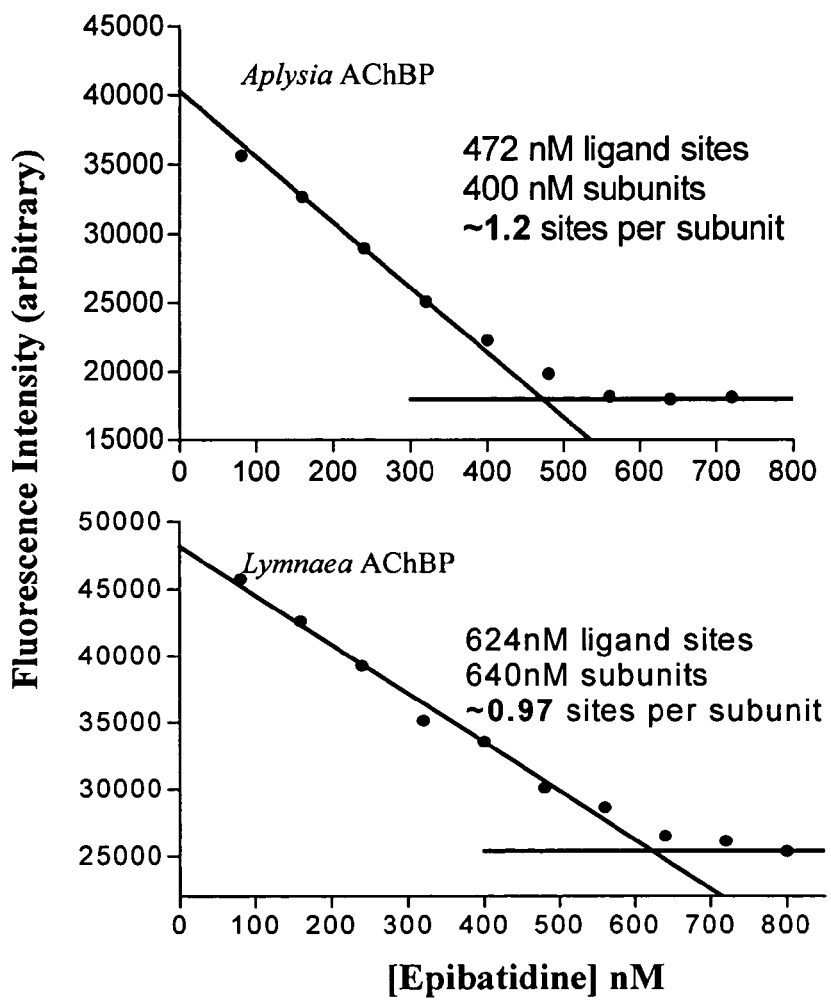
FIGS. 6A and 6B show titration of ligand stoichiometry using excess ligand binding sites over $K_d$ and monitoring intrinsic tryptophan fluorescence quenching of *Aplysia* AChBP (FIG. 6A) and *Lymnaea* AChBP (FIG. 6B) at 340 nm. Binding site titration with ($^3$H)-epibatidine was used to estimate the total number of binding sites. Saturation occurs at approximately 5 sites per pentamer.

Ligand Binding Properties—To determine ligand recognition properties of A-AChBP, an equilibrium-binding assay using intrinsic tryptophan fluorescence of AChBPs was employed. FIG. 6 shows typical mass action curves of both L-AChBP and A-AChBP. While only gallamine enhanced tryptophan fluorescence for L-AChBP, small cholinergic agonists such as choline, acetylcholine and carbachol enhanced fluorescence emission of A AChBP in addition to gallamine. Agonists, such as nicotine and epibatidine, containing ring nitrogens markedly quenched fluorescence of both AChBPs.

Binding of ligands with a $K_d$ less than about 100 nM was monitored using stopped-flow spectrometry and fluorescence detection (Table 4). Table 3 shows a summary of dissociation constants determined from tryptophan fluorescence either by equilibrium titration for lower affinity ligands or by kinetic analysis for the high affinity ligands. Interestingly α-bungarotoxin had a 100 fold lower affinity for A-AChBP than for L-AChBP, whereas the smaller peptide, α-conotoxin ImI, had an affinity for A-AChBP that is more than 4 orders of magnitude greater than that for L-AChBP. Higher affinity of α-conotoxin ImI for *Aplysia* arises primarily from its more rapid dissociation rate (Table 4). The slow binding, high affinity ligands appeared to show a second unimolecular phase of low amplitude for tryptophan fluorescence quenching. As previously reported, L-AChBP has five binding sites per pentamer (34); equilibrium titrations of A-AChBP at concentrations above its $K_d$ likewise revealed five sites per pentamer (FIG. 5). Titration profiles were very similar to those for the L-AChBP.

Table 3 (below) shows dissociation constants for ligand binding to the *Aplysia* and *Lymnaea* AChBPs. The $K_d$ for high affinity ligands[1] ($K_d$'s<100 nM) was determined from the ratio of association and dissociation rates by monitoring intrinsic tryptophan quenching with stopped-flow spectrofluorimetry. Lower affinity ligands were measured using equilibrium fluorescence quenching in a 96 well fluorescent plate reader. All constants are either an average of two values or the mean of three or more. Values varied by less than 20%. [3]Previously reported in the scientific literature (34).

TABLE 3

| Ligand | Aplysia $K_d$ (nM) | Lymnaea $K_d$ (nM) | $K_d$ Ratio L/A |
|---|---|---|---|
| α-Conotoxin ImI | 0.88[1] | 14,000[1] | 16,000 |
| Methyllycaconitine | 2.8[1] | 0.41[3] | 0.14 |
| Epibatidine | 14[1] | 0.16[3] | 0.011 |
| Strychnine | 15[1] | 23[1] | 1.5 |
| Gallamine | 120[2] | 140[3] | 1.2 |
| (−)-Nicotine | 245[2] | 86[3] | 0.35 |
| α-Bungarotoxin | 250[2] | 1.8[3] | 0.0071 |
| Dansylcholine $C_6$ | 1,600[2] | 110[3] | 0.069 |
| Acetylcholine | 33,000[2] | 890[2] | 0.027 |
| Carbachol | 240,000[2] | 5,600[2] | 0.023 |

Table 4 (below) shows kinetic constants for association ($k_1$) and dissociation ($k_{−1}$) of various ligands for the AChBPs. Kinetic constants were determined using stopped-flow spectrofluorimetry. Samples were excited with 280 nm light and emission monitored above 305 nm. Slow dissociation rates of high affinity ligands were measured by competition. Addition of gallamine induced an enhancement of fluorescence in formation of its complex. Data are averages of two measurements or means of three or more measurements.

TABLE 4

| | $k_1$ (×10$^8$ M$^{-1}$s$^{-1}$) | | $k_{-1}$ (s$^{-1}$) | |
|---|---|---|---|---|
| Ligand | Aplysia | Lymnaea | Aplysia | Lymnaea |
| α-Conotoxin ImI | 0.16 | 0.014 | 0.01 | 19 |
| Epibatidine | 2.5 | 1.7 | 3.4 | 0.027 |
| Strychnine | 3.0 | 0.93 | 4.6 | 2.2 |
| Methyllycaconitine | 0.44 | 0.13 | 0.12 | 0.005 |
| Gallamine | 2.5 | 2.5 | 65 | 36 |
| α-Bungarotoxin | 0.010 | 0.009 | 0.32 | 0.001 |
| (−)-Nicotine | 2.3 | 1.5 | 49 | 5.7 |

The discovery of an acetylcholine binding protein from the fresh water mollusk *Lymnaea stagnalis*, and the elucidation of its structure by X-ray crystallography have added a new dimension to the study of the structure and ligand binding properties of the family of nicotinic acetylcholine receptors and related pentameric ligand gated ion channels (3). Moreover, linking structural details of the extracellular domain from crystallography at 2.8 Å resolution to electron microscopy reconstruction analysis of the transmembrane domain of the nAChR at 4 Å has yielded a more comprehensive structural perspective of the nicotinic receptor as an integral unit (1,3,33,36).

The multiplicity of the family of nicotinic receptor subunits and the diversity of subtypes that can be achieved through subunit assembly allow the rank ordering of selective ligands with respect to receptor subtype. The very size of the nAChR family exceeds the discrimination capacity of its ligands precluding a receptor subtype classification based solely on ligand specificity. Nevertheless, ligand selectivity of receptor subtypes allows studies of subtype distribution in regional tissue areas and during developmental processes (37). Developing a complement of AChBPs with distinct specificities can allow the addition of a structural dimension to the analysis of the determinants of ligand specificity, since the soluble proteins and their complexes can be analyzed in far more structural detail.

To this end, a cDNA encoding an AChBP from *Aplysia californica* was synthesized, and the AChBP was demonstrated to assemble as a pentamer, to have a stoichiometry of one ligand binding site per subunit or five per pentamer, and to exhibit a general profile of ligand binding affinities characteristic of the nAChR. The capacity of the expressed *Aplysia* subunit to assemble as a stable pentamer was compared with *Lymnaea*, and a signature ligand was identified for the *Aplysia* AChBP ortholog, wherein α-conotoxin ImI has 16,000-fold greater affinity for *Aplysia* over the *Lymnaea* protein. Other naturally occurring ligands of peptidic or alkaloid composition also show preferential affinities for one or the other AChBPs. α-Conotoxin ImI is produced by the cone snail, *Conus imperialis*, a worm hunting cone snail (38). This conotoxin is known to be a selective ligand for the α7 subtype among the nAChR's (39), indicating that the *Aplysia* AChBP provides a useful model of the α7 receptor subtype, which binds α-conotoxin ImI with a Kd of about 220 nM (see Johnson et al., supra, 1995). The *Aplysia* and *Lymnaea* AChBPs show 26 and 24% residue identity with the extracellular region of α7.

Synthesis, Assembly and Stability of the Acetycholine Binding Protein—Using a mammalian expression system and cDNAs constructed from oligonucleotides designed to introduce restriction sites at strategic locations and weighted towards a mammalian codon abundance resulted in the expression and export of AChBP into the culture medium in quantities of several milligrams per liter. To increase the surface area of attached cells, multilayer 100 cm$^2$ flasks were employed; this expression system should be applicable to other adhesion attachments for cell growth. Multiple media changes and replenishment allowed for continuous production from single plating for up to about one month.

Expression levels of protein differed substantially between experimental constructs depending on the nature of the recognition tag and where it was placed on the construct. A FLAG epitope was used for purification, and a His tag was used for both purification and development of a radioactive assay for the soluble protein. Expression was achieved with both tags, but stability of the protein and the extent of glycosylation processing differed as evidenced by migration on SDS-PAGE. The products of the expression constructs also differed in their capacity to assemble as pentamers as evidenced by size exclusion chromatography and sedimentation analysis. Preparations were routinely monitored to insure that they were virtually devoid of monomeric species and higher orders of assembly or aggregates prior to analyzing binding parameters.

Both AChBPs were purified in quantities of several milligrams, thus allowing for physical investigations of their overall structure in relation to their ligand recognition properties. The purified proteins were quite robust and retained their assembled structure and ligand binding properties for extended periods of time. Of the two, the *Lymnaea* protein appeared to assemble more facilely under the many conditions employed and exhibit the greater stability as measured at extreme pH values. The extent of glycosylation appeared to be dependent on the placement of the recognition tag for purification. Glycosylation also appeared to be an important factor in the ease of crystallization of the two binding proteins.

Determinants of Ligand Specificity—Since the pioneering findings of Karlin and colleagues (40), who demonstrated the importance of vicinal cysteines, now identified in the β9-β10 linker, in the recognition characteristics of the nAChR, elucidating the determinants of recognition for the receptor for the variety of natural and synthetic ligands has become a major endeavor. Studies with site-directed irreversible inhibitors, chemical cross-linking and site-directed mutagenesis all have identified three non-contiguous segments on the face of the α-subunit and four on the opposing face of adjacent subunit of the circular pentamer that harbor the side chain determinants governing ligand specificity (5,41). Identification of these regions and delineation of the characteristics of the residues involved has benefited greatly from the comparison of specificity of homologous subunits, generation of subunit chimeras and site-directed residue substitutions from the homologous or orthologous subunits (5). This approach now can be used with residue substitutions in the homomeric *Lymnaea* and *Aplysia* pair.

The rate constants for association of α-bungarotoxin were far slower than the other ligands suggesting that initial binding of this toxin induces a slow change in conformation or the α-toxin binds to a conformation of low abundance; the slow rates of α-toxin association with the receptor have been long known (42,43). For both α-conotoxin ImI and α-bungarotoxin, differences in affinity for the two AChBP's were reflected primarily in the dissociation rates.

The two AChBP's also differed in several other properties. For example, the *Aplysia* protein has three tryptophans while *Lymnaea* contains an additional tryptophan at position 53 (corresponding to 55 in *Aplysia*). This is a region in the muscle receptor that governs ligand specificity differences seen between the respective binding sites at the αγ, the αε, and the αδ subunit interfaces (5,41). Given the steric requirements for placement of a large indole ethyl side chain, tryptophan at this position becomes a candidate determinant of the distinct affinities found between the *Aplysia* and the *Lymnaea* AChBP's. Moreover, as disclosed herein, many ligands quench the tryptophan fluorescence of the *Lymnaea* protein upon binding; these signals can be exploited further to monitor binding kinetics and ascertain binding orientation of the ligands.

REFERENCES CITED

Each of the following articles is incorporated herein by reference.

1. Karlin, A. (2002) *Nat. Rev. Neurosci.* 3, 102-114.
2. Corringer et al., (2000) *Annu. Rev. Pharmacol. Toxicol.* 40, 431-458.
3. Brejc et al., (2001) *Nature* 411, 269-276.
4. Smit et al., (2001) *Nature* 411, 261-268.
5. Taylor et al., (2000) in *Handbook of Experimental Pharmacology* (Clementi, F., Fornasari, D., and Gotti, C., eds), Vol. 144, pp. 79-100, Springer-Verlag, Berlin.
6. Itakura et al., (1977) *Science* 198, 1056-1063.
7. Lackowicz, J. R. (1999) *Principles of Fluorescence Spectroscopy*, 2 Ed., pp. 185-210, Kluwer Academic/Plenum Publishers, New York.
8. Lockless, S. W., and Ranganathan, R. (1999) *Science* 286, 295-299.
9. Radic, Z., and Taylor, P. (2001) *J. Biol. Chem.* 276, 46224633.
10. Sussman et al., (1991) *Science* 253, 872-879.
11. Galzi et al. (1991) *FEBS Lett.* 294, 198-202.
12. Xie, Y., and Cohen, J. B. (2001) *J. Biol. Chem.* 276, 2417-2426.
13. Beene et al., (2002) *Biochemistry* 41, 10262-10269.
14. Zhong et al. (1998) *Proc. Natl. Acad. Sci. U.S.A.* 95, 12088-12093.
15. Colquhoun, D., and Sakmann, B. (1985) *J. Physiol. (Lond.)* 369, 501-557.
16. Figl et al., (1996) *J. Gen. Physiol.* 107, 369-379.
17. Bouzat et al., (2000) *J. Gen. Physiol.* 115, 663-672.
18. Prince, R. J., and Sine, S. M. (1998) *Biophys. J.* 75, 1817-1827.
19. Salamone, F. N., Zhou, M., and Auerbach, A. (1999) *J. Physiol. (Lond.)* 516, 315-330.
20. Grosman, C., and Auerbach, A. (2001) *Proc. Natl. Acad. Sci. U.S.A.* 98, 14102-14107.
21. Wang et al., (1997) *J. Gen. Physiol.* 109, 757-766.
22. Unwin et al., (2002) *J. Mol. Biol.* 319, 1165-1176.
23. Wenningmann, I., and Dilger, J. P. (2001) *Mol. Pharmacol.* 60, 790-796.
24. Weiland et al., (1977) *J. Biol. Chem.* 252, 7648-7656.
25. Brockes, J. P., and Hall, Z. W. (1975) *Biochemistry* 14, 2092-2099.
26. Wang, G. K., and Schmidt, J. (1980) *J. Biol. Chem.* 255, 11156-11162.
27. Flanagan et al., (1976) *J. Biol. Chem.* 251, 858-865.
28. Mandell et al., (2001) *Protein Eng.* 14, 105-11.
29. Sixma, T. K., and Smit, A. B. (2003) *Annu Rev Biophys Biomol Struct* 32, 311-334.
30. Chang, C. C., and Lee, C. Y. (1963) *Arch Int Pharmacodyn Ther* 144, 241-257.
31. Lee, C. Y. (1963) *Showa Igakkai Zasshi* 23, 221-229.
32. Changeux et al., (1970) *Proc Natl Acad Sci USA* 67, 1241-1247.
33. Miyazawa et al., (2003) *Nature* 424, 949-955.
34. Hansen et al., (2002) *J Biol Chem* 277, 4129941302.
35. Nielsen et al., (1997) *Protein Eng* 10, 1-6.
36. Kash et al., (2003) *Nature* 421, 272-275.

Although the invention has been described with reference to the above example, it will be understood that modifications and variations are encompassed within the spirit and scope of the invention. Accordingly, the invention is limited only by the following claims.

---

What is claimed is:

1. A method for identifying an agent that selectively binds to a naturally occurring pentameric ligand-gated ion channel (LGIC), comprising:
   a) providing a mixture comprised of a non-membrane bound soluble LGIC that fluoresces with a test agent, the soluble LGIC having a conformation that provides a binding site that selectively binds a ligand that modulates the naturally occurring pentameric LGIC;
   b) contacting the test agent with the soluble LGIC; and
   c) detecting a change in fluorescence in the mixture, as compared to the absence of the test agent, wherein the change in fluorescence is indicative of selective binding of the test agent to the binding site of the soluble LGIC, thereby identifying the test agent as an agent that selectively binds to the naturally occurring pentameric LGIC.

2. The method of claim 1, wherein the soluble LGIC comprises a soluble nicotinic acetylcholine receptor (nAChR), and wherein said agent selectively binds the nAChR.

3. The method of claim 2, wherein the soluble nAChR comprises an extracellular domain of a nAChR.

4. The method of claim 2, wherein the soluble nAChR comprises a neuronal-type nAChR.

5. The method of claim 2, wherein the soluble LGIC comprises an acetylcholine binding protein (AChBP).

6. The method of claim 5, wherein the AChBP comprises an *Aplysia* AChBP.

7. The method of claim 6, wherein the *Aplysia* AChBP comprises a polypeptide having the amino acid sequence set forth in SEQ ID NO:2 or SEQ ID NO:4, or an nAChR ligand binding peptide portion of said polypeptide.

8. The method of claim 3, wherein the soluble nAChR is a neuronal-type nAChR.

9. The method of claim 5, wherein the AChBP is a *Lymnaea* AChBP.

10. The method of claim 2, wherein the agent comprises an nAChR agonist.

11. The method of claim 2, wherein the agent comprises an nAChR antagonist.

12. The method of claim 1, wherein:
   a) includes providing a plurality of mixtures, each mixture being comprised of a non-membrane bound soluble LGIC, wherein at least one of the mixtures fluoresces with at least one of a plurality of test agents;
   b) includes contacting each of the plurality of test agents with the soluble LGIC from one of the plurality of mixtures;
   c) includes screening each of the mixtures and detecting a change in fluorescence in the at least one mixture, thereby identifying the at least one of the plurality of test agents (Identified Agent) as an agent that binds to the soluble LGIC; and
   the method further comprising:
      (d) contacting the Identified Agent with a membrane-bound LGIC and detecting selective binding of the Identified Agent to the membrane-bound LGIC, thereby identifying the Identified Agent as an agent that selectively binds to a naturally occurring pentameric LGIC in a membrane.

13. The method of claim 12, which comprises contacting the Identified Agent with a cell expressing the membrane bound LGIC.

14. The method of claim 13, wherein the membrane-bound LGIC comprises an endogenous nAChR.

15. The method of claim 14, wherein the cell is a human cell.

16. The method of claim 1, wherein the soluble LGIC comprises a tryptophan residue at a position corresponding to residue 147 of SEQ ID NO:2.

17. The method or claim 1, wherein the test agent comprises a peptide, a polynucleotide, a peptidomimetic, or a small organic molecule.

18. The method of claim 1, wherein the screening to detect a change in fluorescence comprises detecting a change in intrinsic fluorescence of the soluble LGIC.

19. The method of claim 18, wherein detecting the change in intrinsic fluorescence of the soluble LGIC comprises detecting fluorescence quenching of the intrinsic fluorescence due to selective binding of the test agent.

20. The method of claim 1, wherein the soluble LGIC and the test agent comprise a fluorescence resonance energy transfer (FRET) pair having a FRET emission spectrum.

21. The method of claim 20, wherein the soluble LGIC comprises a fluorescence donor and the test agent comprises a fluorescence acceptor.

22. The method of claim 21, wherein the fluorescence acceptor is operatively linked to the test agent.

23. The method of claim 22, wherein the fluorescence acceptor comprises a dansyl moiety.

24. The method of claim 20, wherein the test agent comprises a fluorescence donor and the soluble LGIC comprises a fluorescence acceptor.

25. The method of claim 20, wherein at least one of the FRET pair has been introduced into the soluble LGIC by mutation.

26. The method of claim 1, further comprising contacting the soluble LGIC with a LGIC ligand, wherein the soluble LGIC and the LGIC ligand comprise a fluorescence resonance energy transfer (FRET) pair having a FRET emission spectrum, wherein selective binding of a test agent alters the FRET emission spectrum as compared to the FRET emission spectrum in the absence of the test agent; and wherein screening the soluble LGIC to detect a change in fluorescence in the mixture comprises detecting a change in the FRET emission spectrum.

27. The method of claim 26, wherein the soluble LGIC comprises a fluorescence donor and the LGIC ligand comprises a fluorescence acceptor.

28. The method of claim 27, wherein the fluorescence acceptor fluoresces at substantially the same wavelength as the fluorescence donor, whereby fluorescence is enhanced, and wherein a decreased amplitude in the emission spectrum is detected upon selective binding of the test agent to the soluble LGIC.

29. The method of claim 27, wherein the LGIC ligand comprises gallamine.

30. The method of claim 27, wherein the fluorescence acceptor fluoresces at a different wavelength from the soluble LGIC.

31. The method of claim 27, wherein a shift in an emission spectrum is detected upon selective binding of the test agent to the soluble LGIC.

32. The method of claim 31, wherein a shift in the emission spectrum is detected by detecting an increase in the fluorescence of the fluorescent donor, a decrease in the fluorescence of the fluorescent acceptor, or an increase in the fluorescence of the fluorescent donor and a decrease in the fluorescence of the fluorescent acceptor.

33. The method of claim 1, which is performed in a high throughput format.

34. The method of claim 1, wherein the test agent is one of a plurality of test agents in the mixture.

35. The method of claim 34, wherein the plurality of test agents comprises a combinatorial library of test agent.

36. The method of claim 35, wherein combinatorial library comprises a random library of test agents, a biased library of test agents, a variegated library of test agents, or a combination thereof.

37. A method for identifying an agent that selectively binds an acetylcholine binding protein (AChBP), comprising:
a) providing a mixture comprising a first non-membrane bound soluble AchBP, the first soluble AChBP having a conformation that provides a binding site that selectively binds a ligand that modulates a naturally occurring pentameric LGIC, wherein the binding site binds conotoxin ImI with a dissociation constant less than 250 nanomolar;
b) in an aqueous solution, contacting the first AChBP with a test agent; and
c) detecting a change in fluorescence in the mixture, as compared to the absence of the test agent, wherein the change in fluorescence is indicative of selective binding of the test agent to the binding site of the first soluble AChBP, thereby identifying an agent that selectively binds to the naturally occurring LGIC.

38. The method of claim 37, wherein the AChBP comprises an *Aplysia* AChBP.

39. The method of claim 37, wherein the *Aplysia* AChBP is encoded by a polynucleotide as set forth in SEQ ID NO: 1; SEQ ID NO:3; or SEQ ID NO:5.

40. The method of claim 38, wherein the *Aplysia* AChBP comprises a polypeptide having the amino acid sequence set forth in SEQ ID NO:2 or SEQ ID NO:4.

41. The method of claim 37, wherein the AChBP comprises SEQ ID NO:2, wherein tyrosine at position 55 of SEQ ID NO:2 is substituted with tryptophan.

42. The method of claim 37, in which the screening comprises detecting a change in intrinsic fluorescence of the AChBP.

43. The method of claim 42, wherein the change in intrinsic fluorescence comprises fluorescence quenching.

44. The method of claim 37, wherein the test agent comprises a fluorescent moiety, wherein the AChBP and the test agent comprise a fluorescence energy resonance transfer (FRET) pair having a FRET emission spectrum, and wherein screening the AChBP to detect a change in fluorescence in the mixture comprises detecting a change in the FRET emission spectrum.

45. The method of claim 44, wherein the fluorescent moiety is operatively linked to the test agent.

46. The method of claim 37, further comprising contacting the AChBP with an AChBP ligand comprising a fluorescent moiety, wherein the AChBP and the AChBP ligand comprise a FRET pair having a FRET emission spectrum, wherein selective binding of a test agent alters the FRET emission spectrum as compared to the FRET emission spectrum in the absence of the test agent; and wherein screening the AChBP to detect the change in fluorescence in the mixture comprises detecting a change in the FRET emission spectrum.

47. The method of claim 46, wherein the fluorescent AChBP ligand enhances fluorescence emission of the AChBP.

48. The method of claim 46, wherein the fluorescent AChBP ligand quenches fluorescence emission of the AChBP.

49. The method of claim 37, further comprising contacting the sample with α-conotoxin ImI, and screening the mixture to detect selective binding of a test agent, thereby identifying an agent that competes with the α-conotoxin ImI for AChBP binding.

50. A method as in claim 12, wherein the mixtures comprise an aqueous solution.

51. The method of claim 12 wherein the membrane-bound LGIC is an endogenous LGIC.

52. The method of claim 12, wherein the membrane-bound LGIC is on the surface of a cell having expressed the membrane-bound LGIC.

53. The method of claim 12, wherein the soluble LGIC comprises a fluorescence donor and the test agent comprises a fluorescence acceptor.

54. The method of claim 12, wherein the test agent comprises a fluorescence donor and the soluble LGIC comprises a fluorescence acceptor.

55. The method of claim 12, further comprising contacting the soluble LGIC with a LGIC ligand, wherein the soluble LGIC and the LGIC ligand comprise a fluorescence resonance energy transfer (FRET) pair having a FRET emission spectrum, wherein selective binding of the test agent alters the FRET emission spectrum as compared to the FRET emission spectrum in the absence of the test agent; and wherein detecting a change in fluorescence of the mixture comprises detecting a change in the FRET emission spectrum.

56. A method for identifying an agent that selectively binds to a naturally occurring pentameric ligand-gated ion channel (LGIC), comprising:
   a) providing a mixture comprised of a non-membrane bound soluble LGIC having conformation that provides a binding site capable of selectively binding a ligand that modulates the naturally occurring pentameric LGIC;
   b) contacting a test agent with the soluble LGIC;
   c) detecting a change in fluorescence in the mixture, as compared to the absence of the test agent, wherein the change in fluorescence in the mixture is indicative of selective binding of the test agent to the soluble LGIC;
   d) preparing a combinatorial library of molecules from the test agent; and
   e) contacting at least one molecule from the combinatorial library with a membrane-bound LGIC and detecting selective binding of the at least one molecule to the membrane-bound LGIC, thereby identifying the at least one molecule as an agent that selectively binds to a naturally occurring pentameric LGIC.

57. A method as in claim 56, wherein the step of preparing a combinatorial library comprises preparing a phage display library of peptides, a peptide library, a peptidomimetic library, a nucleic acid library, an oligosaccharide library, a lipoprotein library, a glycoprotein library, a glycolipid library, a small molecule library, or a combination thereof.

58. The method of claim 1, further comprising:
   d) preparing a combinatorial library of molecules from the test agent; and
   e) contacting at least one molecule from the combinatorial library with a membrane-bound LGIC under conditions suitable for selective binding of a LGIC ligand to the membrane-bound LGIC and screening the at least one molecule in the presence of the membrane-bound LGIC to detect selective binding of the at least one molecule to the membrane-bound LGIC, thereby identifying the at least one molecule as an agent that selectively binds to a membrane-bound pentameric LGIC.

59. A method as in claim 1, wherein the binding site selectively binds an agonist, antagonist, and/or partial agonist to the naturally occurring pentameric LGIC.

60. A method as in claim 37, wherein the binding site selectively binds an agonist, antagonist, and/or partial agonist to the naturally occurring pentameric LGIC.

61. A method as in claim 12, wherein the binding site selectively binds an agonist, antagonist, and/or partial agonist to the naturally pentameric LGIC.

62. A method as in claim 56, wherein the binding site selectively an agonist, antagonist, and/or partial agonist to the pentameric LGIC.

* * * * *